US010201459B2

(12) United States Patent
Yamamoto et al.

(10) Patent No.: US 10,201,459 B2
(45) Date of Patent: Feb. 12, 2019

(54) METHOD FOR MANUFACTURING ABSORBENT ARTICLE

(71) Applicant: UNICHARM CORPORATION, Ehime (JP)

(72) Inventors: Hiroki Yamamoto, Kagawa (JP); Yoshihiko Matsumoto, Kagawa (JP)

(73) Assignee: Unicharm Corporation, Ehime (JP)

( * ) Notice: Subject to any disclaimer, the term of this patent is extended or adjusted under 35 U.S.C. 154(b) by 226 days.

(21) Appl. No.: 15/113,554

(22) PCT Filed: Jan. 8, 2015

(86) PCT No.: PCT/JP2015/050336
§ 371 (c)(1),
(2) Date: Jul. 22, 2016

(87) PCT Pub. No.: WO2015/129296
PCT Pub. Date: Sep. 3, 2015

(65) Prior Publication Data
US 2017/0007467 A1 Jan. 12, 2017

(30) Foreign Application Priority Data

Feb. 28, 2014 (JP) ................................ 2014-038866

(51) Int. Cl.
*A61F 13/15* (2006.01)
*A61F 13/49* (2006.01)
(Continued)

(52) U.S. Cl.
CPC .. *A61F 13/15593* (2013.01); *A61F 13/15723* (2013.01); *A61F 13/15739* (2013.01);
(Continued)

(58) Field of Classification Search
CPC .......... A61F 13/15593; A61F 13/15577; A61F 13/15739; A61F 13/49; A61F 13/496
See application file for complete search history.

(56) References Cited

U.S. PATENT DOCUMENTS

2010/0096065 A1* 4/2010 Yamamoto ........ A61F 13/15739
156/73.4

FOREIGN PATENT DOCUMENTS

JP 2001-333932 A 12/2001
JP 2004-229857 A 8/2004
(Continued)

OTHER PUBLICATIONS

International Search Report from corresponding PCT application No. PCT/JP2015/050336 dated Apr. 7, 2015 (4 pgs).
(Continued)

*Primary Examiner* — Mark A Osele
*Assistant Examiner* — Christopher C Caillouet
(74) *Attorney, Agent, or Firm* — Brinks Gilson & Lione

(57) ABSTRACT

A method for manufacturing an absorbent article, the method including: while a lower bandlike member is transported in a transport direction, a process in which a cutting position is determined and an adhesion area is formed on each side of the cutting position of the lower bandlike member in the transport direction; a process in which leg elastic members are placed so that a part of each of the leg elastic members overlaps the adhesion area, the leg elastic members being stretched in a direction having a component parallel to the transport direction; a process in which an upper bandlike member is stacked on and adheres to the lower bandlike member and the leg elastic member on the adhesion area; a process in which the lower bandlike member and the upper bandlike member are folded on the center in the intersecting direction; a process in which a welded
(Continued)

section on which the lower bandlike member and the upper bandlike member are to be welded to each other is formed on each side of the cutting position in the transport direction; a process in which and the lower bandlike member, the upper bandlike member and the leg elastic members are cut together on the cutting position, a lower exterior member and an upper exterior member which are shaped in the form of underpants are cut and separated, the leg elastic members which are stretched contract towards the adhesion area from positions at which the leg elastic members are cut, the contraction being performed while the leg elastic members shifting relative to the lower exterior member and the upper exterior member.

5 Claims, 13 Drawing Sheets

(51) Int. Cl.

| | | |
|---|---|---|
| *A61F 13/496* | (2006.01) | |
| *B29C 53/04* | (2006.01) | |
| *B29C 55/02* | (2006.01) | |
| *B29C 65/08* | (2006.01) | |
| *B29C 65/48* | (2006.01) | |
| *B29C 69/00* | (2006.01) | |
| *B29K 105/08* | (2006.01) | |
| *B29L 31/48* | (2006.01) | |

(52) U.S. Cl.
CPC ............ *A61F 13/49* (2013.01); *A61F 13/496* (2013.01); *B29C 53/04* (2013.01); *B29C 55/02* (2013.01); *B29C 65/08* (2013.01); *B29C 65/4815* (2013.01); *B29C 69/001* (2013.01); *B29K 2105/0809* (2013.01); *B29K 2995/0046* (2013.01); *B29K 2995/0068* (2013.01); *B29L 2031/4878* (2013.01)

(56) References Cited

FOREIGN PATENT DOCUMENTS

| | | |
|---|---|---|
| JP | 2009-189621 A | 8/2009 |
| JP | 2013-126527 A | 6/2013 |
| WO | WO 01/72237 A2 | 10/2001 |
| WO | WO 2007/123445 A1 | 11/2007 |
| WO | WO 2011/081032 A1 | 7/2011 |
| WO | WO 2011/105475 A1 | 9/2011 |
| WO | WO 2012/087209 A1 | 6/2012 |
| WO | WO 2012/087210 A1 | 6/2012 |
| WO | WO 2013/094591 A1 | 6/2013 |

OTHER PUBLICATIONS

European Supplementary Search Report from corresponding European application No. 15754825.6 dated Nov. 22, 2016 (7 pgs).

* cited by examiner

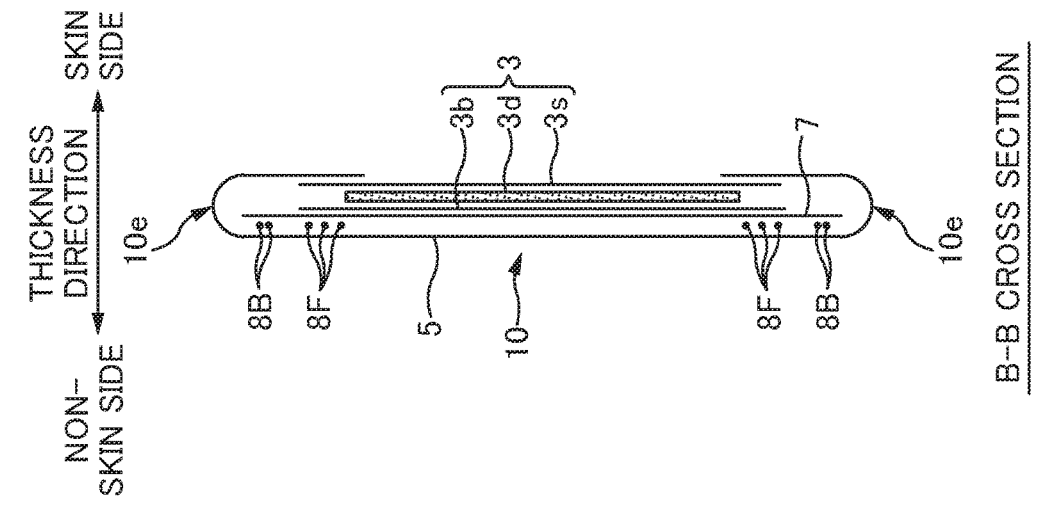
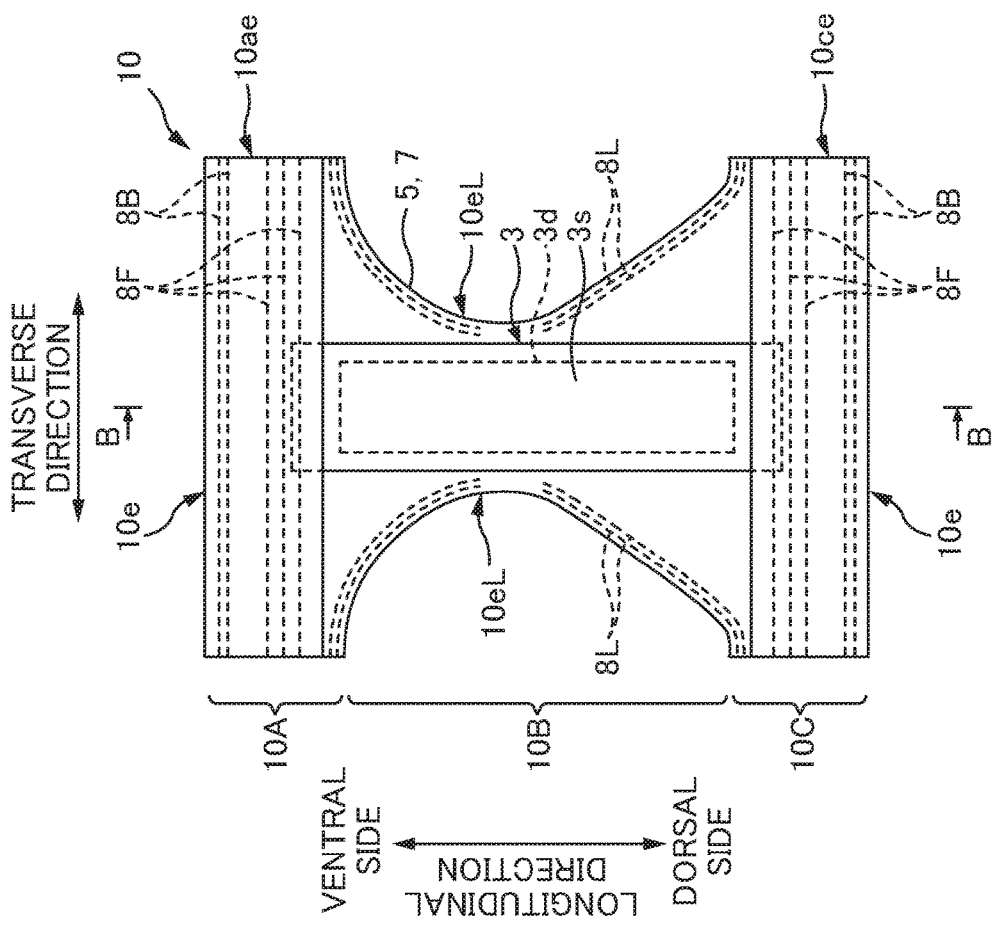
FIG. 1B
FIG. 1A

METHOD FOR MANUFACTURING ABSORBENT ARTICLE

RELATED APPLICATION

The present application is a 35 U.S.C. § 371 national stage filing of International Patent Application No. PCT/JP2015/050336, filed Jan. 8, 2015, to which priority is claimed under 35 U.S.C. § 120 and through which priority is claimed under 35 U.S.C. § 119 to Japanese Priority Patent Application No. 2014-038866, filed Feb. 28, 2014.

TECHNICAL FIELD

The invention relates to a method for manufacturing an absorbent article.

BACKGROUND ART

In a manufacturing line for absorbent articles such as a disposable diaper, the following method is commonly used for manufacturing pull-on diapers: the end sections of the continuous sheet in the transverse direction are folded to be layered on a ventral part and on a dorsal part while the continuous sheet is transported in the transport direction, the continuous sheet being to be an exterior material of a disposable diaper, the transport direction being a direction in which the continuous sheet continues; then, both end sections of the continuous sheet are each joined; and thereafter a single-cut piece is cut and separates from the continuous sheet. For example, Patent Literature 1 discloses a method for manufacturing a pull-on diaper as follows: elastic members which are disposed being stretched in the transport direction of the continuous sheet (a ventral part and a dorsal part) are divided at certain intervals in the transport direction; and the ventral part and the dorsal part which are stacked are heat-sealed (welded) on the divided areas. And then, the ventral part and the dorsal part are cut and separated on the sealed areas.

CITATION LIST

Patent Literature

[Patent Literature 1] Japanese Patent Application Laid-open Publication No. 2013-126527

SUMMARY OF THE INVENTION

Technical Problem

In Patent Literature 1, before a welding process and a cutting-and-separating process, the elastic members are divided in advance so as to produce contract force; this makes it possible to prevent the welded area from contracting together with the elastic members when cutting the elastic members. This makes it possible to manufacture a diaper which has a good appearance and keeps up soft feeling on the side sealings thereof. But, in this method, when dividing the elastic member, the continuous sheet which is to be the exterior materials of the diapers is likely to be damaged by tools such as a cutter. If the damaged continuous sheet is heat-welded, it is possible that sufficient welding strength cannot be ensured on the damaged part.

In the method of Patent Literature 1, a problem concerning leg elastic members provided along the leg openings of a diaper may occur. For example, low fitting of the leg openings causes a gap between a wearer's legs and the leg openings when a diaper is worn. In order to prevent excrement leakage from such a gap, the leg elastic members are provided so as to produce stretching/contraction force which is greater than that produced by other elastic members; that is, the leg elastic members are provided being stretched so as to be subjected to greater stress than other elastic members. This improves the fitting of the leg openings of a diaper. But, if the leg elastic members are divided on the welded section as in Patent Literature 1, this may make the leg elastic members to be less likely to be held on the continuous sheet. As a result, the leg elastic members are removed from the leg openings of a diaper, and this is likely to make the fitting of the leg openings worse.

In view of the problem described above, it is an advantage of the invention to provide a pull-on diaper in which the welding strength of the side parts thereof is sufficient and the leg elastic members thereof are less likely to be removed.

Solution to Problem

An aspect of the invention to achieve the above advantage is a method for continuously manufacturing an absorbent article,
the absorbent article being a pull-on absorbent article that has a longitudinal direction and a transverse direction intersecting the longitudinal direction, and
that include
a lower exterior member located on a side towards a wearer's garment,
an upper exterior member stacked on the lower exterior member from a side towards a wearer's skin,
an absorbent main body stacked on the upper exterior member from the side towards a wearer's skin, for absorbing excrement,
the method, including:
while a lower bandlike member and an upper bandlike member are transported in a transport direction that is along the transverse direction,
the lower bandlike member including the lower exterior members that continue in a band-like manner in the transverse direction,
the upper bandlike member including the upper exterior members that continues in a band-like manner in the transverse direction,
a process in which, when the lower exterior member and the upper exterior member are cut and separated from the lower bandlike member and the upper bandlike member,
a cutting position is determined, and
an adhesion area is formed by putting adhesive on each side of the cutting position in the transport direction, of at least either one of the lower bandlike member and the upper bandlike member,
the cutting position being to serve as end sections of the lower exterior member and the upper exterior member in the transverse direction;
a process in which
a plurality of leg elastic members are placed on at least either one of the lower bandlike member and the upper bandlike member so that a part of each of the leg elastic members overlaps the adhesion area, the leg elastic members being stretched in a direction having a component parallel to the transport direction, the leg elastic members being provided along a leg opening of the pull-on absorbent article;

a process in which the lower bandlike member and the upper bandlike member are stacked such that the leg elastic members being sandwiched between the lower and upper bandlike members, and the upper bandlike member adheres to the lower bandlike member and the leg elastic members on the adhesion area;

a process in which the lower bandlike member and the upper bandlike member are folded on a center portion in an intersecting direction so that the upper bandlike member is located inside the lower bandlike member, the intersecting direction intersecting the transport direction;

a process in which a welded section on which the folded lower bandlike member and the folded upper bandlike member are to be welded to each other is formed on each side of the cutting position in the transport direction;

a process in which the lower bandlike member, the upper bandlike member and the leg elastic members are cut together on the cutting position, the lower exterior member and the upper exterior member which are shaped in the form of underpants are cut and separated from the lower bandlike member and the upper bandlike member, at least some of the plurality of leg elastic members that are stretched in the direction having the component parallel to the transport direction contract in the transport direction towards the adhesion area from positions at which the at least some of the plurality of leg elastic members are cut, the contraction being performed while the at least some of the plurality of leg elastic members shifting relative to the lower exterior member and the upper exterior member.

Other features of this invention will become apparent from the description in this specification and the attached drawings.

Effects of the Invention

According to the invention, it is possible to provide a pull-on diaper in which the welding strength of the side parts thereof is sufficient and the leg elastic members thereof are less likely to be removed.

BRIEF DESCRIPTION OF THE DRAWINGS

FIG. 1A is a plan view of a disposable diaper 1 which is spread out. FIG. 1B is a cross-sectional view taken along line B-B in FIG. 1A.

MODE FOR CARRYING OUT THE INVENTION

Figure 2:
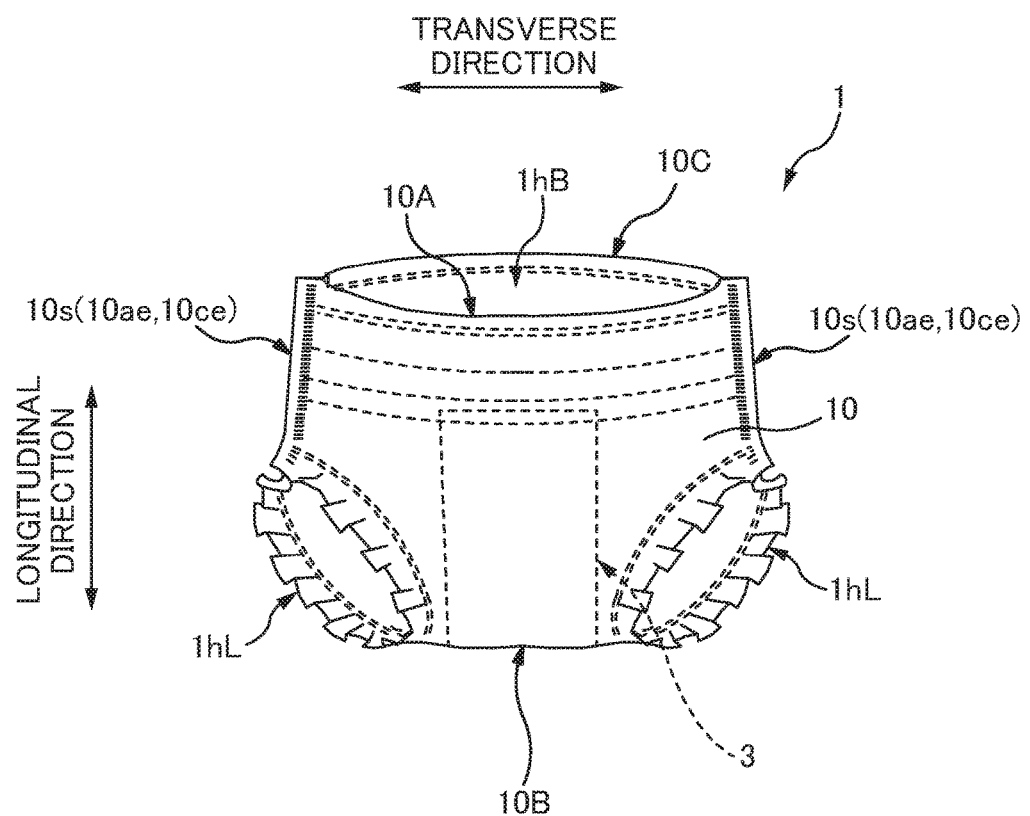
FIG. 2 is a schematic perspective view of a diaper 1 which is shaped in the form of underpants.

At least the following matters will be made clear by the description in the present specification and the accompanying drawings.

A method for continuously manufacturing an absorbent article, the absorbent article being a pull-on absorbent article that has a longitudinal direction and a transverse direction intersecting the longitudinal direction, and that include a lower exterior member located on a side towards a wearer's garment, an upper exterior member stacked on the lower exterior member from a side towards a wearer's skin, an absorbent main body stacked on the upper exterior member from the side towards a wearer's skin, for absorbing excrement, the method, including:

while a lower bandlike member and an upper bandlike member are transported in a transport direction that is along the transverse direction, the lower bandlike member including the lower exterior members that continue in a band-like manner in the transverse direction, the upper bandlike member including the upper exterior members that continues in a band-like manner in the transverse direction, a process in which, when the lower exterior member and the upper exterior member are cut and separated from the lower bandlike member and the upper bandlike member, a cutting position is determined, and an adhesion area is formed by putting adhesive on each side of the cutting position in the transport direction, of at least either one of the lower bandlike member and the upper bandlike member, the cutting position being to serve as end sections of the lower exterior member and the upper exterior member in the transverse direction;

a process in which
- a plurality of leg elastic members are placed on at least either one of the lower bandlike member and the upper bandlike member so that a part of each of the leg elastic members overlaps the adhesion area,
  - the leg elastic members being stretched in a direction having a component parallel to the transport direction,
  - the leg elastic members being provided along a leg opening of the pull-on absorbent article;

a process in which
- the lower bandlike member and the upper bandlike member are stacked such that the leg elastic members being sandwiched between the lower and upper bandlike members, and
- the upper bandlike member adheres to the lower bandlike member and the leg elastic members on the adhesion area;

a process in which
- the lower bandlike member and the upper bandlike member are folded on a center portion in an intersecting direction so that the upper bandlike member is located inside the lower bandlike member,
  - the intersecting direction intersecting the transport direction;

a process in which
- a welded section on which the folded lower bandlike member and the folded upper bandlike member are to be welded to each other is formed on each side of the cutting position in the transport direction;

a process in which
- the lower bandlike member, the upper bandlike member and the leg elastic members are cut together on the cutting position,
- the lower exterior member and the upper exterior member which are shaped in the form of underpants are cut and separated from the lower bandlike member and the upper bandlike member,
- at least some of the plurality of leg elastic members that are stretched in the direction having the component parallel to the transport direction contract in the transport direction towards the adhesion area from positions at which the at least some of the plurality of leg elastic members are cut,
  - the contraction being performed while the at least some of the plurality of leg elastic members shifting relative to the lower exterior member and the upper exterior member.

With such a method for manufacturing an absorbent article, it is possible to manufacture a pull-on diaper in which the welding strength of the side parts thereof is sufficient and the leg elastic members thereof are less likely to be removed.

In such a method for manufacturing an absorbent article, it is desirable that the welded section does not overlap the adhesion area within at least a partial area along the transport direction.

With such a method for manufacturing an absorbent article, an area in which the adhesion area and the welded section do not overlap is formed. This can prevent the following phenomena: welding strength of the welded section is insufficient due to the oil of adhesive which forms adhesion area; and the number of maintenance operations of a welding device increase due to putting of adhesive.

In such a method for manufacturing an absorbent article, it is desirable that a distance between the cutting position and one end section of the welded section in the transport direction is shorter than a distance between the cutting position and one end section of the adhesion area in the transport direction, the one end section of the welded section being closer to the cutting position than the other end section is, the one end section of the adhesion area being closer to the cutting position than the other end section is.

With such a method for manufacturing an absorbent article, the welded section is more likely to be formed at a position closer to a cutting position CL in the transport direction than the adhesion area is. As for the elastic members that have contracted when cutting and separating the substrate at the cutting position, end sections thereof are held on the welded section between the cutting position and the adhesion area and become less likely to be noticeable. This makes it possible to prevent impairing the appearance of the elastic members on the side areas of the diaper.

In such a method for manufacturing an absorbent article, it is desirable that the welded section is formed at intervals along the intersecting direction.

With such a method for manufacturing an absorbent article, the leg elastic members enter between two adjacent welded sections and become more likely to be held while being sandwiched between the lower bandlike member and the upper bandlike member. Accordingly, the leg elastic members are less likely to be removed from the bandlike member, and this can prevent stretchability of the leg openings of the diaper from being lost.

In such a method for manufacturing an absorbent article, it is desirable that a distance between two welded sections that are formed adjacent in the intersecting direction is larger than a diameter of each of the elastic members.

With such a method for manufacturing an absorbent article, each elastic member is more likely to enter between two adjacent welded sections. This makes it easier to prevent deterioration of the appearance of the diaper on the side areas and to ensure sufficient welding strength.

In such a method for manufacturing an absorbent article, it is desirable that a plurality of the adhesion areas are formed being aligned in the transport direction along the position on which the leg elastic member is placed.

With such a method for manufacturing an absorbent article, it will often be possible that, when the leg elastic member contracts in the transport direction, any of the plurality of adhesion areas formed being aligned in the transport direction stop the contraction of the leg elastic member. Accordingly, the leg elastic member is less likely to be removed from the leg openings of the diaper. This can prevent the fitting of the leg openings of a diaper from being lost.

In such a method for manufacturing an absorbent article, it is desirable that the process in which the adhesion area is formed is performed by placing the leg elastic members on at least either one of the lower bandlike member and the upper bandlike member, adhesive being applied to the leg elastic members on a certain area while the leg elastic members being stretched in a direction having a component parallel to the transport direction.

With such a method for manufacturing an absorbent article, applying the adhesive to the elastic members increases adhesion of the elastic members on the adhesion area compared to the cases where the adhesive is not applied to the elastic members. This makes it easier to prevent problems such as elastic drop-off. Further, the process in which the adhesion area is formed and the process in which the elastic members are placed are simultaneously performed, and this allows the absorbent articles to be efficiently manufactured.

In such a method for manufacturing an absorbent article, it is desirable that the leg elastic members are cut at a single position located between a pair of the adhesion areas, the leg elastic members being stretched in the direction having the component parallel to the transport direction, the adhesion areas being respectively formed on both side of the cutting position in the transport direction, and that the leg elastic members contract in the transport direction towards the adhesion areas from positions at which the leg elastic members are cut.

With such a method for manufacturing an absorbent article, the elastic member is not finely divided, but are cut at a single position. This can prevent a plurality of pieces of the divided elastic member from remaining in the side parts of a diaper as foreign objects and can also prevent pieces of the divided elastic member from extending beyond the side parts of a diaper. This makes the appearance of the diaper better in the side parts thereof.

In such a method for manufacturing an absorbent article, it is desirable that the adhesive is not put on an area between the cutting position and the adhesion area.

With such a method for manufacturing an absorbent article, when the elastic members are cut at the cutting position, the elastic members that have been cut are more likely to perform cut-back. Accordingly, stretching/contraction force by the elastic members is not exerted in the side areas of the diaper. This makes it possible to prevent the appearance of the diaper from deteriorating due to contraction of the side areas.

In such a method for manufacturing an absorbent article, it is desirable that the adhesive is put on an area between the cutting position and the adhesion area, and that an amount per unit area of the adhesive that is to be put on an area between the cutting position and the adhesion area is smaller than an amount per unit area of the adhesive that is to be put on the adhesion area.

With such a method for manufacturing an absorbent article, when the elastic members are cut at the cutting position, the elastic members that have been cut perform cut-back. Stretching/contraction force by the elastic members is thereby not exerted in the area between the cutting position and the adhesion area. This makes it possible to prevent the appearance of the diaper from deteriorating due to contraction of the side areas of the diaper.

First Embodiment

<Basic Configuration of Diaper 1>

As an example of an absorbent article manufactured in a manufacturing method of the present embodiment, a pull-on disposable diaper (hereinafter referred to as a diaper 1) is employed and the basic configuration thereof will be described first. FIG. 1A is a plan view of a diaper 1 which is spread out and FIG. 1B a cross-sectional view taken along line B-B in FIG. 1A. FIG. 2 is a schematic perspective view of a diaper 1 which is shaped in the form of underpants.

As shown in FIGS. 1A and 1B, the diaper 1 which is spread out has the longitudinal direction, the transverse direction (a direction which intersects the longitudinal direction) and the thickness direction (a direction which intersects the longitudinal direction and the transverse direction). The diaper 1 includes the following components: a lower exterior member 5 (herein also referred to as an outer back) located on the side towards a wearer's garment; an upper exterior member 7 (herein also referred to as an outer top) which is stacked in the thickness direction on and is joined to the lower exterior member 5 from the side towards a wearer's skin; and a liquid-absorbent, absorbent main body 3 which is stacked in the thickness direction on and is joined to the upper exterior member 7 from the side towards the wearer's skin, and which absorbs excrement such as urine.

The lower exterior member 5 and the upper exterior member 7 are flexible stretchable members in the form of sheet, and are made of materials such as nonwoven fabric. As shown in FIG. 1B, the longitudinal length of the lower exterior member 5 is longer than the longitudinal length of the upper exterior member 7, and the diaper 1 which is spread out has a configuration in which the upper exterior member 7 is folded back on longitudinal edge sections 10e to wrap the longitudinal end areas of the absorbent main body 3. In the following description, the lower exterior member 5 and the upper exterior member 7 which is stacked on the lower exterior member 5 are collectively referred to as an exterior member 10.

The exterior member 10 forms the contour of diaper 1 in the spread-out state, and the planar shape thereof is a substantially hourglass shape (see FIG. 1A). That is, the exterior member 10 (the lower exterior member 5 and the upper exterior member 7) has a shape in which the transverse edges are narrowed transversely inwardly in the longitudinal central section. The exterior member 10 is divided along the longitudinal direction as follows: a ventral part 10A that covers a wearer's abdomen; a crotch part 10B that covers a wearer's crotch; and a dorsal part 10C that covers a wearer's back. The diaper 1 which is spread out is two-folded on a substantially center in the longitudinal direction, and the ventral part 10A and the dorsal part 10C are connected on the transverse edges. Thereby, a pull-on diaper 1 having the waist opening 1hB and a pair of leg openings 1hL and 1hL shown in FIG. 2 is formed.

The absorbent main body 3 is in a substantially rectangular shape when viewed from above. The absorbent main body 3 is placed in the center of the transverse direction, and the lengthwise direction of the absorbent main body 3 is along the longitudinal direction of the diaper 1. The absorbent main body 3 does not have to be in a rectangular shape shown in FIG. 1A, and may be, for example, a substantially hourglass shape similar to the exterior member 10. The absorbent main body 3 includes: an absorbent body 3d which absorbs and holds fluid; a liquid-permeable top face sheet 3s which wraps the absorbent body 3d from a wearer's skin side and through which excrement such as urine passes; and a liquid-impermeable back face sheet 3b made of materials such as film which wraps the absorbent body 3d from the non-skin side and which prevents fluid leakage from the non-skin side. The absorbent body 3d is made by shaping fluid-absorbent fiber such as pulp fiber into a certain shape such as a substantially rectangular parallelepiped. And, the absorbent body 3d contains superabsorbent polymer therein. The absorbent body 3d may be covered with tissue paper. Further, upstanding gather (leak-proof cuff) for preventing side leakage may be provided on both transverse edges of the absorbent main body 3.

On appropriate positions in the exterior member 10, a plurality of the elastic members 8B, 8F, 8L . . . , which are made of rubber thread and the like, are placed between the lower exterior member 5 and the upper exterior member 7. These elastic members 8B, 8F, 8L . . . are for providing stretchability to a diaper 1. For example, in the longitudinal edge sections 10e and 10e of the exterior member 10, a plurality of the waist elastic members 8B and 8B are respectively disposed along the transverse direction; the longitudinal edge sections 10e and 10e are respectively an edge section 10*e* which forms the waist opening 1*h*B in the ventral part 10A (corresponding to a waist-circumference edge section) and an edge section 10*e* which forms the waist opening 1*h*B in the dorsal part 10C (corresponding to a waist-circumference edge section). These waist elastic members 8B and 8B are stretched in the transverse direction and partial areas thereof adhere and are fixed to the lower exterior member 5 and the upper exterior member 7. And stretchability is thereby provided to the waist opening 1*h*B, which is composed of the edge sections 10*e* and 10*e*. Similarly, a plurality of fitting-gather elastic members 8F, 8F, . . . are disposed along the transverse direction at the position near the center in the longitudinal direction with respect to the positions of the waist elastic members 8B. These fitting-gather elastic members 8F, 8F, . . . are stretched in the transverse direction. And, partial areas of thereof adhere and are fixed to the lower exterior member 5 and the upper exterior member 7. Stretchability in the transverse direction is thereby provided to parts between the waist opening 1*h*B and the longitudinal center.

In addition, a plurality of the leg elastic members 8L, 8L, . . . are respectively disposed of edge sections 10*e*L and 10*e*L of the transverse edge sections of the exterior member 10, the edge sections 10*e*L and 10*e*L being to form the leg openings 1*h*L. These leg elastic members 8L, 8L, . . . are stretched along the edge sections 10*e*L and 10*e*L. And, partial areas of thereof adhere and are fixed to the lower exterior member 5 and the upper exterior member 7. That is, the leg elastic members 8L, 8L, . . . are held by the exterior member 10 while being stretched in the longitudinal direction and in the transverse direction, as shown in FIG. 1A. Stretchability is thereby provided to the exterior member 10 along the edge sections 10*e*L and 10*e*L, which are to form the leg openings 1*h*L and 1*h*L. Note that the leg elastic members 8L produce greater stretching/contraction force in the leg opening 1*h*L because the leg elastic members 8L are disposed while being stretched more strongly than the waist elastic members 8B and the fitting-gather elastic members 8F. By increasing the stretchability of the leg openings 1*h*L, the fitting on a wearer's legs when a diaper 1 is worn increases, and a gap between a wearer's legs and the leg openings 1*h*L becomes less likely to be formed. This can prevent the occurrence of problems such as excrement leakage to outside the diaper 1 from a gap between a wearer's legs and the leg openings 1*h*L.

A pull-on diaper shown in FIG. 2 is shaped by folding back the crotch part 10B of the exterior member 10 near the longitudinal center and by joining (sealing) the transverse end section 10*ae* of the ventral part 10A and the transverse end section 10*ce* of the dorsal part 10C. These joined transverse end section 10*ae* and transverse end section 10*ce* are to be the end sections 10*s* of the diaper 1 shown in FIG. 2.

<Method for Manufacturing Diaper 1>

A method for manufacturing diapers 1 associated with the present embodiment will be described.

Figure 3:
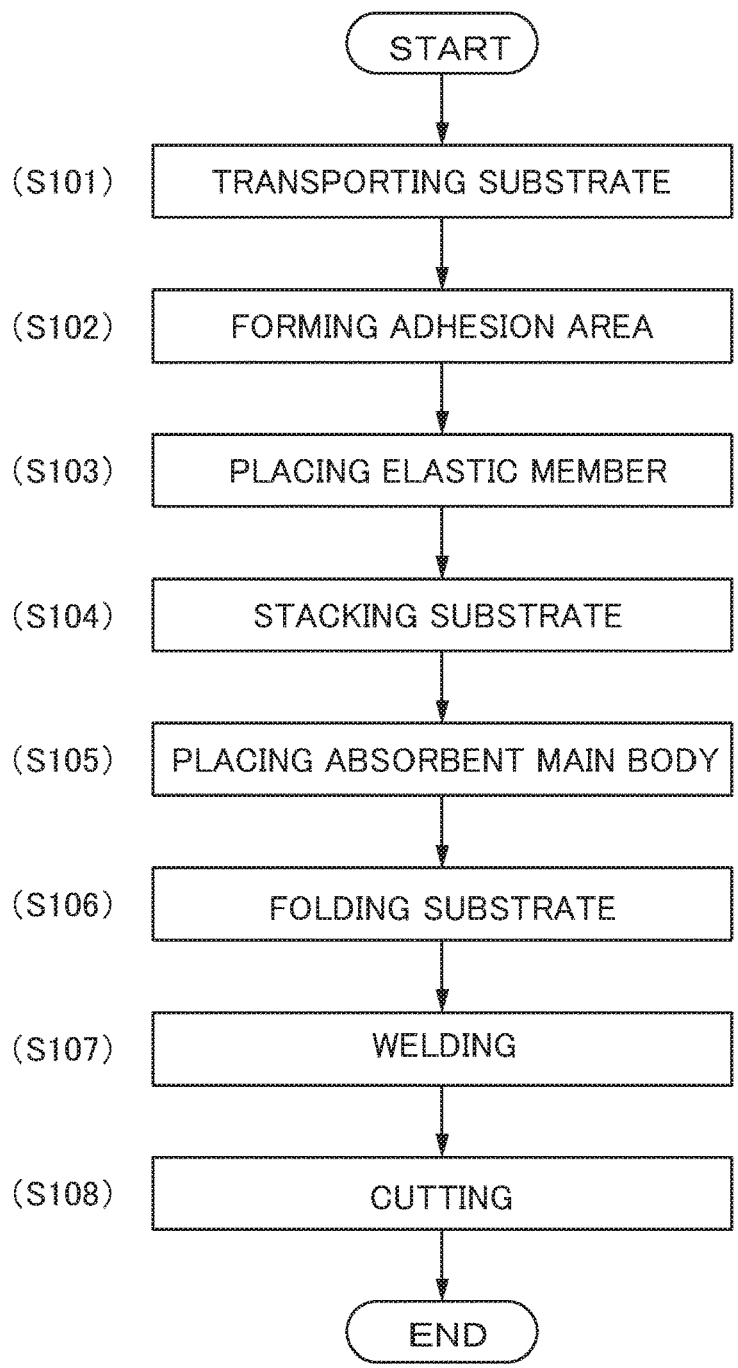
FIG. 3 is a flow chart of processes for manufacturing diapers 1 of the first embodiment.

FIG. 3 is a flow chart of processes for manufacturing diapers 1 of the first embodiment. The diapers 1 are continuously manufactured by performing the processes represented by the symbols S101 to S108 of the manufacturing line of the diapers 1 in FIG. 3. The processes will be sequentially described below.

In the manufacturing line of the diaper 1, the substrate of the diapers 1 is transported by a suitable transport mechanism along a certain transport direction at a certain transport speed (S101).

The "substrate of the diapers 1" herein means a band-like member in which a plurality of the lower exterior members 5 (or the upper exterior members 7) shown in FIG. 1A are continuously linked in the transverse direction. Hereinafter, the band-like member in which the lower exterior members 5 continue in the transverse direction is referred to as a lower bandlike member 15, and the band-like member in which the upper exterior member 7 continue in the transverse direction is referred to as an upper bandlike member 17. "The transport direction" is a direction along the transverse direction of the exterior member 10 in FIG. 1A. In the following description, a direction which intersects the transport direction (that is, a direction along the longitudinal direction of the exterior member 10) is referred to as the "intersecting direction". In the first embodiment, the processes S102 to S108 are performed while the lower bandlike member 15 (or the upper bandlike member 17) is transported in the transport direction.

Figure 4:
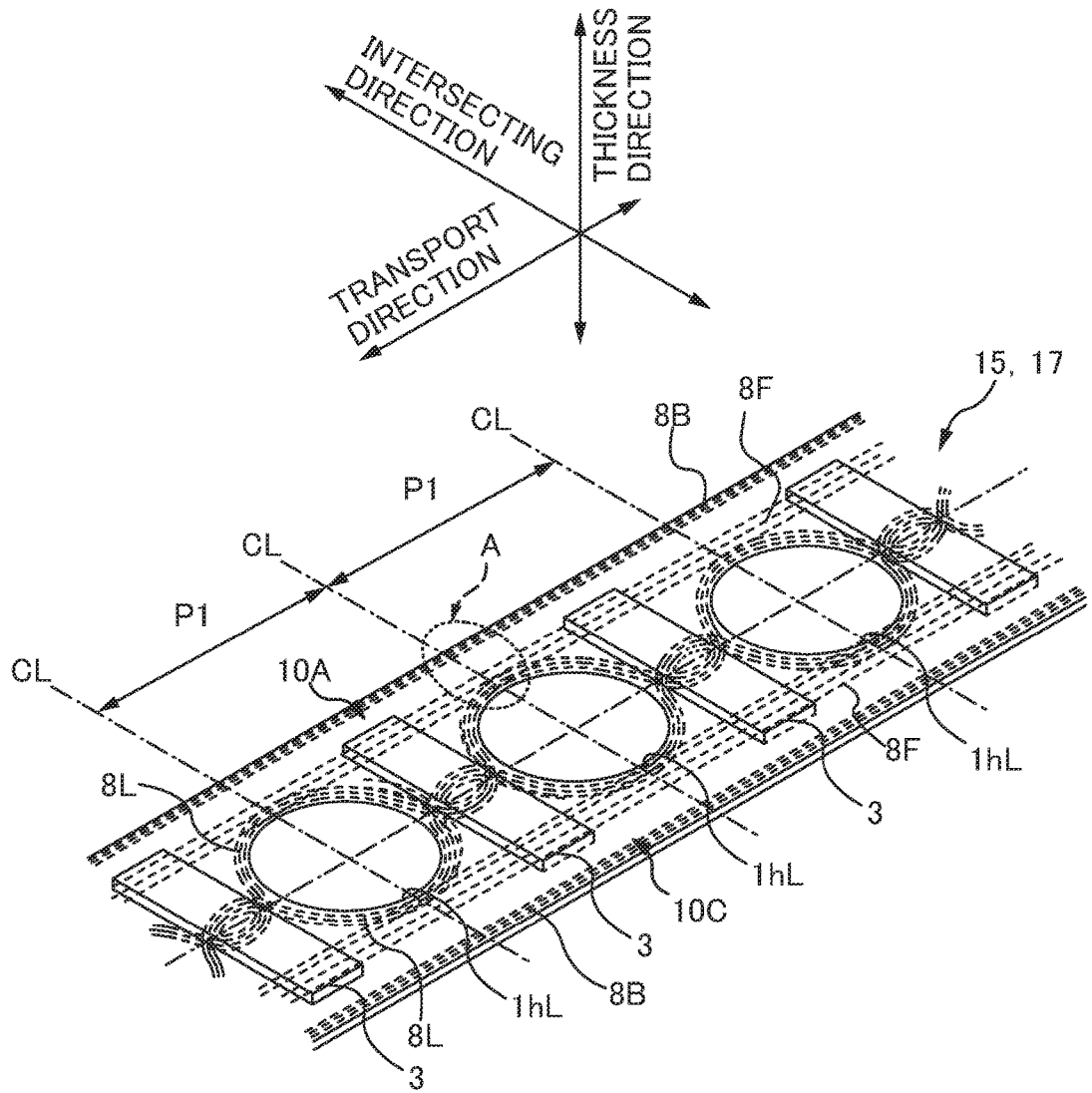
FIG. 4 is a diagram illustrating how the substrate of the diapers 1 is transported in the transport direction.

FIG. 4 is a diagram illustrating how the substrate of the diapers 1 is transported in the transport direction. FIG. 4 shows how the lower bandlike member 15, the upper bandlike member 17, the elastic members 8B, 8F, and 8L and the absorbent main body 3 are transported in the processes of S101 to S105; the lower bandlike member 15 and the upper bandlike member 17 are stacked such that the elastic members 8B, 8F, and 8L are sandwiched between them, and the absorbent main body 3 is joined thereon. The following section describes how the elastic members 8B, 8F, and 8L and the upper bandlike member 17 are stacked onto the lower bandlike member 15 which is being transported. But, it is also acceptable that the upper bandlike member 17 is transported and the lower bandlike member 15, etc. are stacked onto the upper bandlike member 17 which is being transported.

The lower bandlike member 15 is transported in the transport direction in a state where the lower exterior members 5 which are adjacent to each other in the transport direction (the transverse direction) continue on a cutting position CL. The cutting position CL is a reference position when the lower exterior member 5 (the exterior member 10) is cut and separates from the lower bandlike member 15 in the following cutting process (S108). That is, the cutting position CL is a position on which a cutting line is formed, the cutting line being for cutting diapers 1 from the bandlike member into a single piece, and also the cutting position CL is for serving as the end sections 10*s* of a diaper 1 which is shaped in the form of underpants (see FIG. 2). Also, the cutting line is a reference position in the following adhesion-area forming process (S102) and welding process (S107). In the present embodiment, the operations of the processes are controlled based on the cutting position CL. The cutting positions CL are determined at intervals (pitches) P1 in the transport direction. The interval P1 corresponds to the transverse length of the ventral part 10A and the dorsal part 10C of the exterior member 10 when the ventral part 10A and the dorsal part 10C have not been contracted yet.

While the lower bandlike member 15 being transported, the leg openings 1*h*L are formed. The leg openings 1*h*L are formed in an area extending in the transport direction and being centered on the cutting position CL, and are each indicated as the edge section 10*e*L of the exterior member 10 in FIG. 1A. In the present embodiment, the leg openings 1*h*L are formed using a cutting device (not shown) at the same time as the position of the cutting position CL has been determined or at a certain timing thereafter.

Figure 5A:
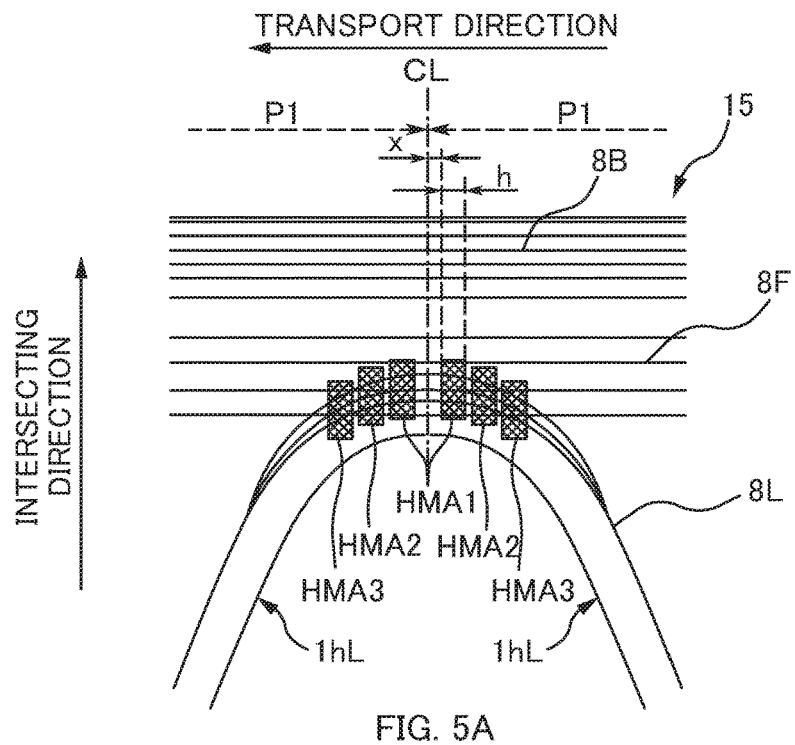
FIGS. 5A and 5B are diagrams illustrating sections where an adhesion area is formed.
Figure 5B:
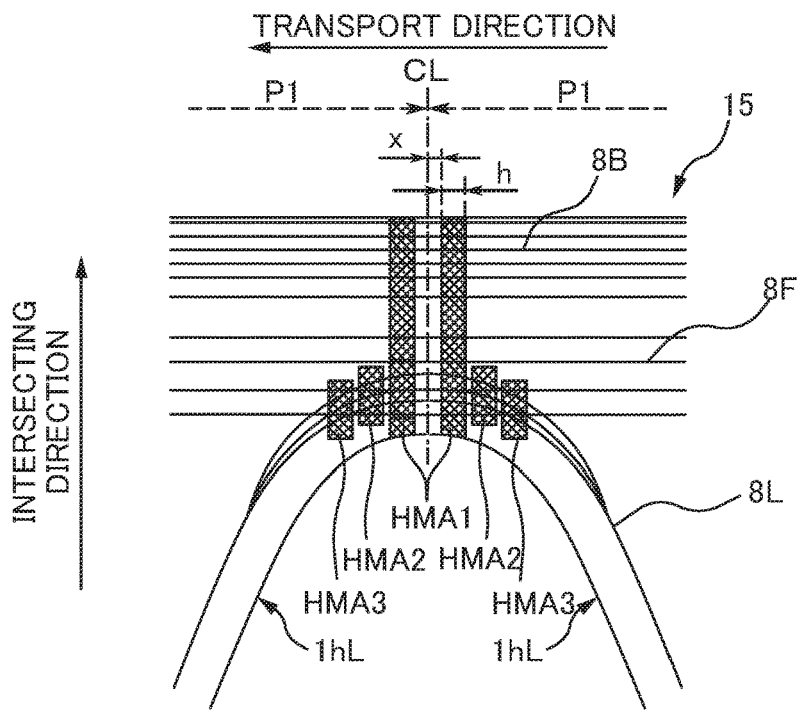

Next, adhesion areas are formed by putting adhesive onto certain areas on the lower bandlike member 15 which is being transported in the transport direction (S102). FIGS. 5A and 5B are diagrams illustrating sections where the adhesion areas are formed. FIGS. 5A and 5B are magnified views of the area A in FIG. 4. Though the elastic members 8B, 8F, and 8L are placed on the lower bandlike member 15 in FIGS. 5A and 5B, the elastic members will be placed in the next process (S103) in the present embodiment. Accordingly, when adhesive is put on the lower bandlike member 15 in the adhesion-area forming process S102, the elastic members 8B, 8F, and 8L have not placed on the lower bandlike member 15 yet. Hot-melt type adhesive is used as an example of the adhesive, and the adhesion areas are formed by applying adhesive to the certain areas on the lower bandlike member 15 using an adhesive coater (not shown).

In the present embodiment, the adhesion areas are formed in a certain area on both sides, in the transport direction, of the cutting position CL of the lower bandlike member 15 (or the upper bandlike member 17). Specifically, as shown in the hatched parts of FIG. 5A, the rectangular adhesion areas HMA1, HMA2, and HMA3 are formed in the form of pair respectively, along the area in which the leg openings 1hL are formed about the cutting position CL. In other words, a plurality of the adhesion areas are formed along the position on which the leg elastic members 8L are placed. Since the adhesion areas are formed along the leg openings 1hL, the leg elastic members 8L are joined to the lower bandlike member 15 (or the upper bandlike member 17) in the area, and the leg elastic members 8L become more likely to be held.

The adhesion area HMA1 is an area having a width of h in the transport direction, and is formed at a distance x in the transport direction from a cutting position CL. In the present embodiment, it is desirable that the value x are approximately within the range from 5 mm to 15 mm. That is, it is desirable that the adhesion areas HMA are not formed (adhesive is not applied) within the range between 10 mm and 30 mm from the cutting position CL in the transport direction. This reason will be described later. On the other hand, the width h of the adhesion area HMA1 is not particularly limited, and the adhesion area HMA1 may be narrower or wider than that shown in FIG. 5A. The adhesion area HMA2 has substantially the same shape as the adhesion area HMA1, and is formed adjacent in the transport direction to the adhesion area HMA1. The adhesion area HMA3 has substantially the same shape as the adhesion area HMA1 and the adhesion area HMA2, and is formed adjacent in the transport direction to the adhesion area HMA2. These three adhesion areas HMA1, HMA2 and HMA3 are formed being arranged in the transport direction because, when cutting the leg elastic members 8L in the following cutting process (S108), the leg elastic members 8L contracting in the transport direction are held by the three adhesion areas HMA1, HMA2 and HMA3 so as to be less likely to be removed from the lower bandlike member 15. However, as long as the adhesion areas HMA2 and HMA3 can hold the leg elastic members 8L contracting in the transport direction, the sizes of the adhesion areas HMA2 and HMA3 may be arbitrary, and may be smaller or larger than the adhesion area HMA1. In addition, the number of the adhesion areas which are formed is arbitrary; for example, the adhesion area HMA1 alone may be formed without the adhesion areas HMA2 and HMA3.

FIG. 5B shows an example of other shape of an adhesion area formed in the present embodiment. In FIG. 5B, the adhesion area HMA1 has a shape elongated in the intersecting direction. In this case, in the adhesion area HMA1, the leg elastic members 8L are joined to and held by the lower bandlike member 15 (or the upper bandlike member 17), and also the waist elastic members 8B and the fitting-gather elastic members 8F can be joined and held. The adhesion areas HMA2 and HMA3 may have a shape elongated in the intersecting direction like the adhesion area HMA1, or may have any other shape. In the following description, the adhesion areas HMA1 to HMA 3 are collectively referred to as "the adhesion areas HMA".

In the foregoing description, the adhesion areas HMA are formed on the lower bandlike member 15 by putting adhesive on the lower bandlike member 15. However, the adhesion areas HMA may be formed on the upper bandlike member 17 by putting adhesive on the upper bandlike member 17. Also, the adhesion areas HMA may be formed on both members by putting adhesive on both of the lower bandlike member 15 and the upper bandlike member 17.

After the adhesion areas HMA are formed, the elastic members 8B, 8F, and 8L are placed (S103).

Figure 6A:
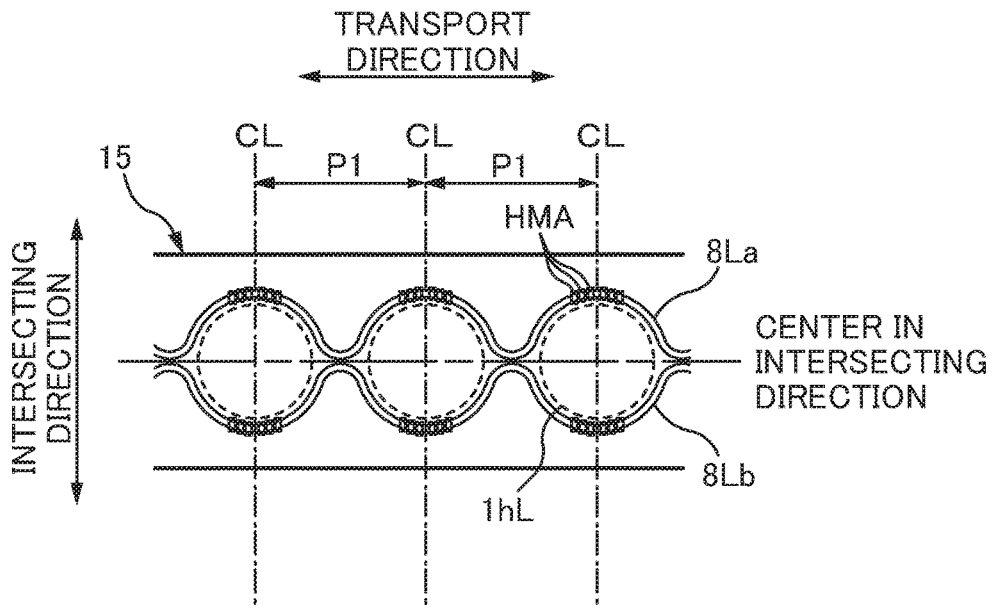
FIGS. 6A and 6B are schematic diagrams illustrating how the leg elastic members 8L are placed.
Figure 6B:
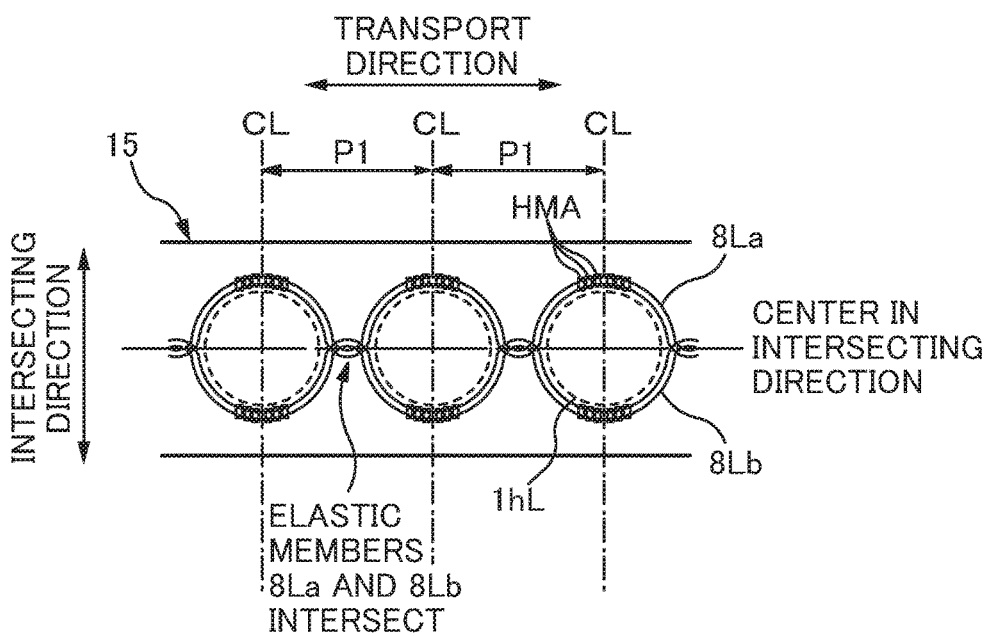

FIGS. 6A and 6B are schematic diagrams illustrating how the leg elastic members 8L are placed. In the present embodiment, a plurality of leg elastic members 8L are placed along the position on which a leg opening 1hL of the lower bandlike member 15 (the upper bandlike member 17) is formed. Placing the leg elastic members 8L is performed using a known oscillating device (not shown). While moving back and forth in the intersecting direction, the oscillating device introduces the leg elastic members 8L to the lower bandlike member 15 (the upper bandlike member 17) which is being transported in the transport direction; at this stage, the leg elastic members 8L which are stretched. In the example of FIG. 6A, a leg elastic member 8La is introduced so as to draw a meandering pattern (e.g., sine curve) in an area which is upper than the center of the lower bandlike member 15 in the intersecting direction. Similarly, a leg elastic member 8Lb is introduced in a meandering pattern (e.g., sine curve) into an area which is lower than the center of the intersecting direction. At that time, at least partial areas of leg elastic members 8La and 8Lb are placed so as to overlap the adhesion areas HMA which are formed in S102. Thus, the leg elastic members 8L are placed along the position on which the leg opening 1hL is formed. Further, the leg elastic member 8La and the leg elastic member 8Lb may be placed so that the leg elastic members 8La and 8Lb intersect in partial areas. In the examples of FIG. 4 and FIG. 6B, the leg elastic member 8La and the leg elastic member 8Lb are placed so as to intersect near the middle between cutting positions CL and CL adjacent in the transport direction.

Thus, the leg elastic members 8L are placed being stretched along the position on which the leg opening 1hL is formed (that is, being stretched in a direction having a component parallel to the transport direction), and the leg elastic members 8L are joined to the lower bandlike member 15 (the upper bandlike member 17) through the adhesion areas HMA. Note that adhesive may be applied directly to the leg elastic members 8L as follow.

As shown in FIGS. 5A and 5B, while being stretched in the transport direction, a plurality of the waist elastic members 8B are placed in an area of each end section of the lower bandlike member 15 (the upper bandlike member 17) in the intersecting direction. Similarly, while being stretched in the transport direction, a plurality of the fitting-gather elastic members 8F are placed in an inner area of the lower bandlike member 15 (the upper bandlike member 17) with respect to each end section in the intersecting direction. In FIG. 5A, the adhesion areas HMA are formed along an area in which the leg elastic members 8L are placed, but no adhesion area HMA is formed in an area in which the waist elastic members 8B and the fitting-gather elastic members 8F are placed. In this case, while the waist elastic members 8B and the fitting-gather elastic members 8F are stretched, adhesive is applied to certain areas of the surfaces of the elastic members 8B and 8F. And then, by placing the elastic members 8B and 8F, the elastic members 8B and 8F are joined to the lower bandlike member 15 (the upper bandlike member 17). On the other hand, in FIG. 5B, the waist elastic members 8B and the fitting-gather elastic members 8F are joined to the lower bandlike member 15 (the upper bandlike member 17) through the adhesion area HMA1.

As mentioned above, the leg elastic members 8L are disposed of the lower bandlike member 15 (the upper bandlike member 17) with being stretched more strongly than the waist elastic members 8B and the fitting-gather elastic members 8F. This allows the leg elastic members 8L to produce greater stretching/contraction force in the leg openings 1hL of the diaper 1. It is not necessary for the leg openings 1hL to have been formed at a time when placing the leg elastic members 8L. The leg openings 1hL may be formed after the leg elastic members 8L are placed on the bandlike members.

After the elastic members are placed, the upper bandlike member 17 are stacked on the lower bandlike member 15 and the elastic members 8B, 8F, and 8L which are placed on the lower bandlike member 15 (S104). Then, by pressurizing in the thickness direction so that the upper bandlike member 17 is pressed against the lower bandlike member 15, the upper bandlike member 17 adheres to the lower bandlike member 15 on the adhesion areas HMA. The elastic members 8B, 8F, and 8L are thereby fixed while being sandwiched in the thickness direction between the lower bandlike member 15 and the upper bandlike member 17, and the exterior members of the diapers 1 are formed. The length of the lower bandlike member 15 in the intersecting direction is longer than the length of the upper bandlike member 17 in the intersecting direction, but this is not shown in FIG. 4. Accordingly, at the stage of S104, both end sections of the lower bandlike member 15 in the intersecting direction extend beyond both end sections of the upper bandlike member 17 in the intersecting direction.

In the elastic-member placing process (S103), the elastic members 8B, 8F, and 8L are placed being stretched. And, in this process (S104), these elastic members 8B, 8F, and 8L are sandwiched between and fixed to the lower bandlike member 15 and the upper bandlike member 17. This allows each of the elastic members 8B, 8F, and 8L to produce stretchability in the lower bandlike member 15 and the upper bandlike member 17. For example, the leg elastic members 8L produce stretchability along the leg openings 1hL, and the waist elastic members 8B and the fitting-gather elastic members 8F produce stretchability along the transport direction.

Subsequently, the absorbent main body 3 is placed on and joined to the upper side of the upper bandlike member 17 in the thickness direction, the upper bandlike member 17 being stacked on and adhering to the lower bandlike member 15 (S105). Note that the absorbent main body 3 is separately manufactured in a manufacturing line for absorbent main bodies (not shown). As shown in FIG. 4, the absorbent main body 3 is placed at a position between the cutting positions CL in the transport direction (that is, the transverse central section of the exterior member 10) so that the lengthwise direction of the absorbent main body 3 is in the intersecting direction. And, the absorbent main body 3 is joined to the surface of the upper bandlike member 17 with adhesive and the like. After the absorbent main body 3 is joined, a beyond-edge part of end section of the lower bandlike member 15 in the intersecting direction is bent so as to wrap the absorbent main body 3 from the upper side in the thickness direction (see FIG. 1B). Parts of the lower bandlike member 15 adhere to the absorbent main body 3 and/or the upper bandlike member 17.

Figure 7:
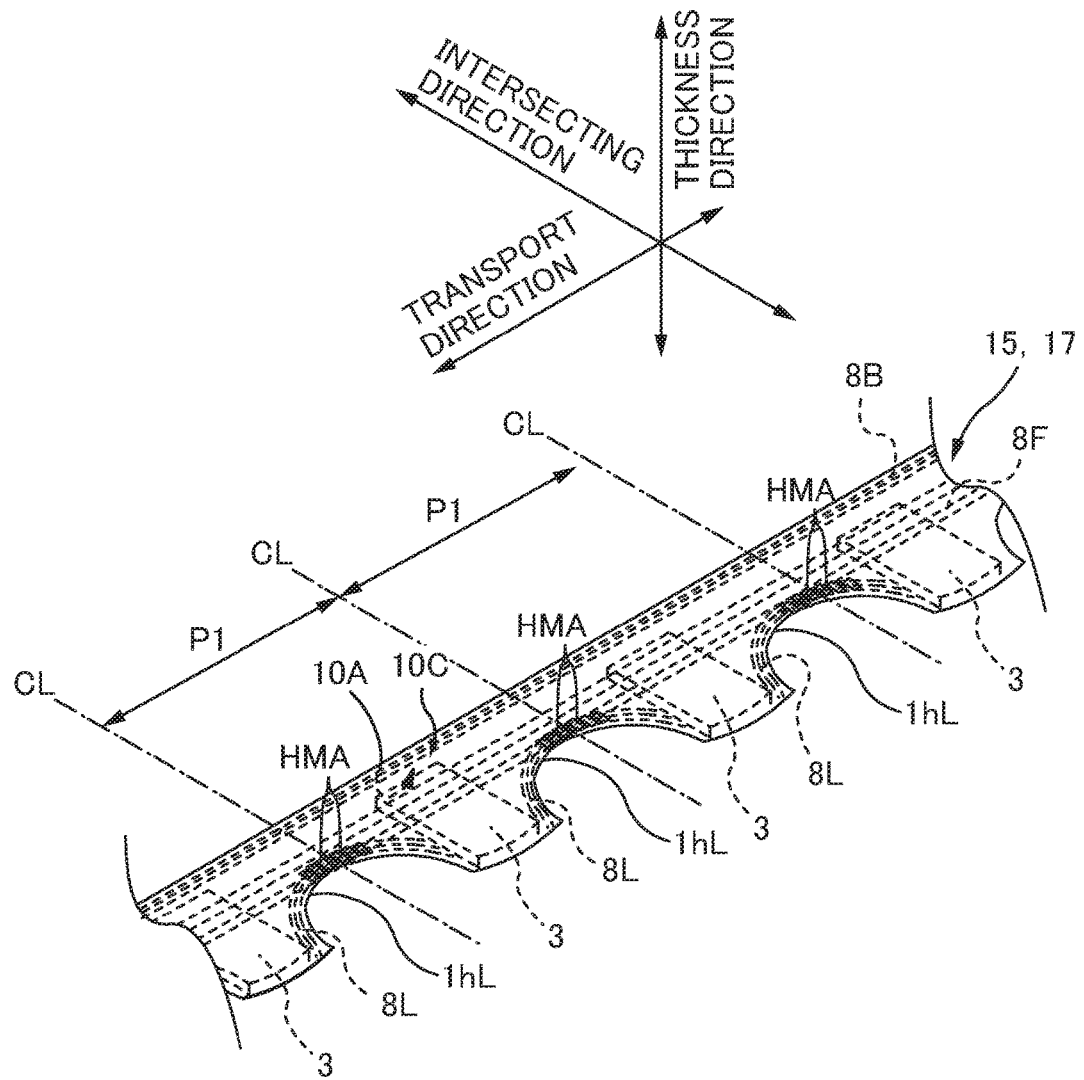
FIG. 7 is a diagram illustrating how the folded substrate of diapers 1 is transported after the process of S105.

Subsequently, the lower bandlike member 15 and the upper bandlike member 17 which are stacked are folded on the center in the intersecting direction so that the upper bandlike member 17 is located inside the lower bandlike member 15 (S106). FIG. 7 is a diagram illustrating how the folded substrate of diapers 1 is transported after the process of S105. As shown in the figure, by folding on the center in the intersecting direction, the ventral part 10A and the dorsal part 10C of the diaper 1 are stacked in the thickness direction and are in a state in which pants-form substrates continue in the transport direction. In this process, the bandlike members and the absorbent main body 3 are merely bent and stacked, and the ventral part 10A and the dorsal part 10C are not joined to each other.

Figure 8:
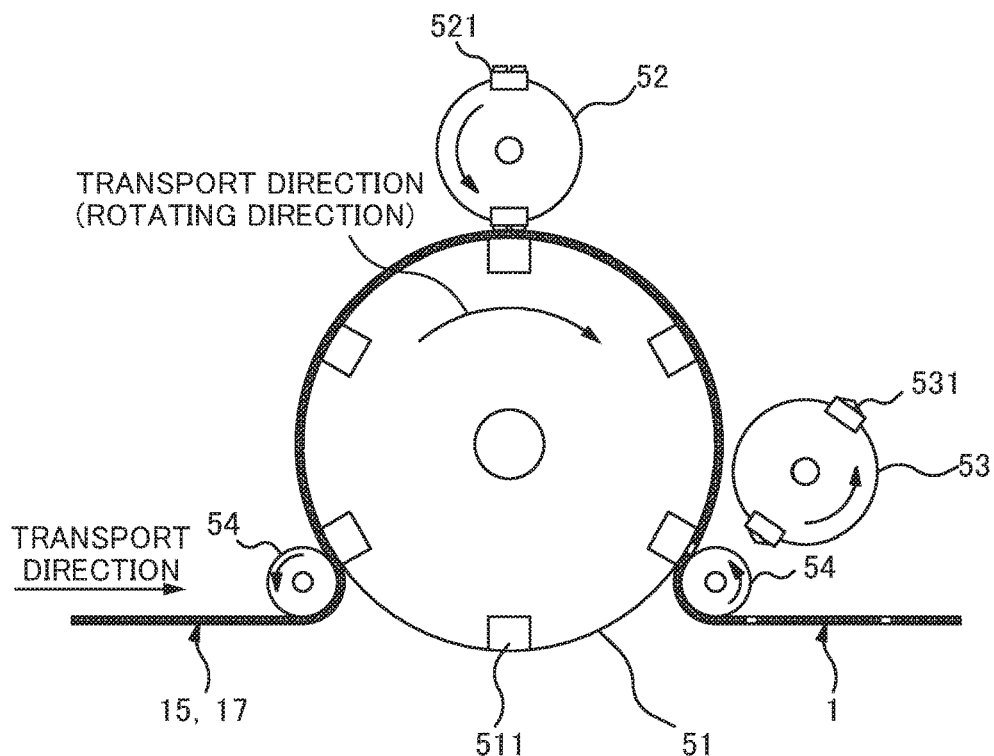
FIG. 8 is a schematic side view of a welding-and-cutting apparatus 50 used in the first embodiment.
Figure 9:
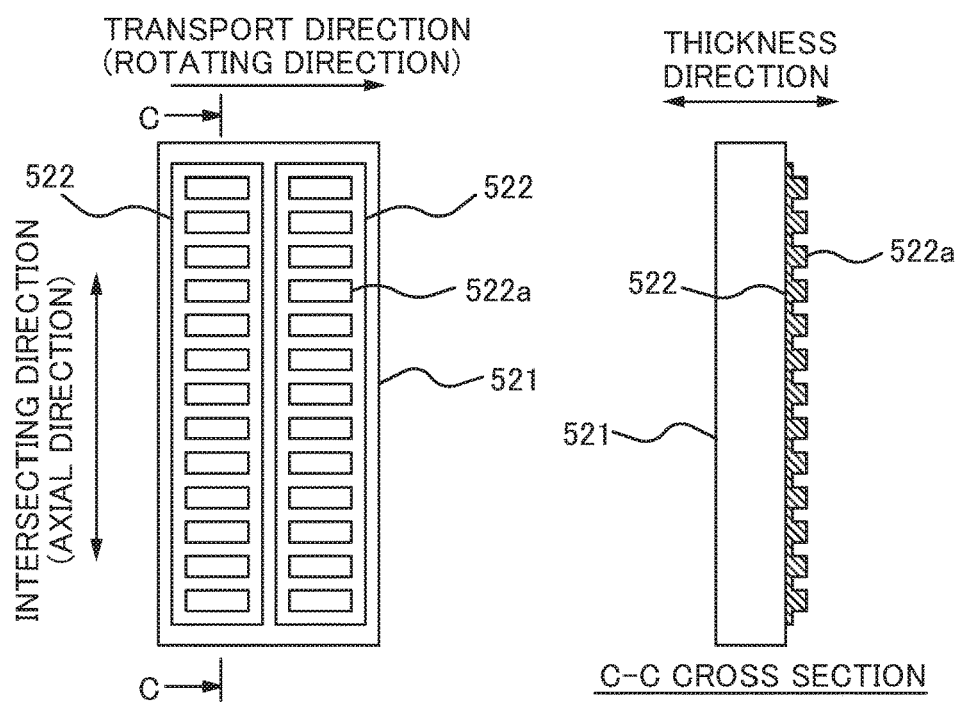
FIG. 9 is a diagram illustrating a sealing block 521 of the welding-and-cutting apparatus 50.

Subsequently, the ventral part 10A and the dorsal part 10C which are stacked are welded onto a certain area (S107). A method of the welding is heat welding or ultrasonic welding. In the following description, an example of heat welding will be described. FIG. 8 is a schematic side view of a welding-and-cutting apparatus 50 used in the manufacturing line of the first embodiment. FIG. 9 is a diagram illustrating sealing block 521 of the welding-and-cutting apparatus 50. With the welding-and-cutting apparatus 50, cutting in the next process (S108) is performed as well as welding of the ventral part 10A and the dorsal part 10C.

The welding-and-cutting apparatus 50 includes: an anvil roll 51; a sealing roll 52; a cutter roll 53; and transportation-assisting rolls 54. The anvil roll 51 is a drum-like rotating body, and has an sucking mechanism (not shown) on the circumferential surface thereof. The anvil roll 51 rotates while the upper bandlike member 17 and the lower bandlike member 15 are sucked on and fixed to the circumferential surface thereof, and thereby the bandlike members 15 and 17 are transported in the rotating direction. On the circumferential surface of the anvil roll 51, a plurality of anvil brocks 511 are provided. Each of the anvil brocks 511 is a member elongated in the axial direction of the anvil roll 51 (corresponding to the foregoing intersecting direction). A substrate can be heat-welded by being sandwiched and heated between the anvil brock 511 and the following sealing block 521 in the direction of the normal of the anvil roll 51 (corresponding to the foregoing thickness direction). In the figure, the anvil brocks 511 are provided in the positions which divide along the circumferential direction the circumference of the anvil roll 51 into six equal parts, but the number of the anvil brocks 511 included in a single anvil roll 51 is not limited to six.

The sealing roll 52 is a rotating body placed at a position facing the anvil roll 51 as shown in FIG. 8. On the circumferential surface of the sealing roll 52 (corresponding to the intersecting direction), the sealing block 521 is provided along the axial direction of the sealing roll 52. These components have a positional relationship in which the anvil brock 511 and the sealing block 521 face periodically by rotation of the anvil roll 51 and simultaneous rotation of the sealing roll 52 in the opposite direction. In the present embodiment, adjustment is made so that the anvil brock 511 and the sealing block 521 face each other at a point-in-time when the bandlike members 15 and 17 are transported by pitch P1 between adjacent two cutting positions in the transport direction. In FIG. 8, though the sealing blocks 521 are provided respectively in the positions which divide along the circumferential direction the circumference of the sealing roll 52 into two equal parts, the number of the sealing blocks 521 is not limited to two. Each of the sealing blocks 521 includes two protruding sections 522 aligned in the rotating direction (the transport direction). On each protruding section 522, a plurality of rectangular portions 522a protruding in the thickness direction are placed at intervals along the axial direction (the intersecting direction). When the rectangular portions 522a face the anvil brock 511 of the anvil roll 51 and come into contact with the substrates, the substrates are heated by the heated rectangular portion 522a and the anvil brock 511. And this makes it possible to heat-weld (heat-seal) the areas corresponding to the rectangular portions 522a. The shape of the rectangular portions 522a is not limited to the example shown in FIG. 8, and does not have to be rectangle. For example, the shape of the rectangular portions 522a may be triangle or circle. In addition, the number of the rectangular portions 522 may change depending on the area of the welding range or welding conditions as appropriate. However, in the present embodiment, it is preferable that a gap between two adjacent rectangular portions 522a in the axial direction (the intersecting direction) (that is, a gap in the intersecting direction) is larger than the diameter of the leg elastic members 8L. This reason will be described later.

The cutter roll 53 is used, in the next cutting process (S108), when cutting the lower bandlike member 15 and the upper bandlike member 17 at the cutting position CL along the intersecting direction. The cutter roll 53 is a rotating body placed at a position facing the anvil roll 51 and downstream from the sealing roll 52 in the transport direction. On the circumferential surface of the cutter roll 53, the cutter block 531 is provided along the axial direction of the cutter roll 53 (corresponding to the intersecting direction). These components have a positional relationship in which the anvil brock 511 and the cutter block 531 faces periodically by rotation of the anvil roll 51 and simultaneous rotation of the cutter roll 53 in the opposite direction. The cutter block 531 includes a cutter (not shown) along the axial direction (the intersecting direction). When the cutter faces the anvil brock 511 of the anvil roll 51 and comes into contact with a substrate, the substrate can be cut in the intersecting direction.

The transportation-assisting rolls 54 are provided upstream and downstream from the anvil roll 51 in the transport direction. The transportation-assisting rolls 54 assist the transportations of the lower bandlike member 15 and the upper bandlike member 17 along the circumferential surface of the anvil roll 51, and adjusts the magnitude of tension which is exerted on the lower bandlike member 15 and the upper bandlike member 17 which are being transported. Uniform tension during transportation makes it possible to prevent the occurrence of faulty weld and/or displacement at the time of welding.

In the foregoing example, heat-welding (heat-sealing) is described. Though the configuration of apparatuses for ultrasonic welding (sonic-sealing) is partly different therefrom (e.g., the sealing block 521 is replaced with ultrasonic horn), the basic operation of welding is the same.

Figure 10:
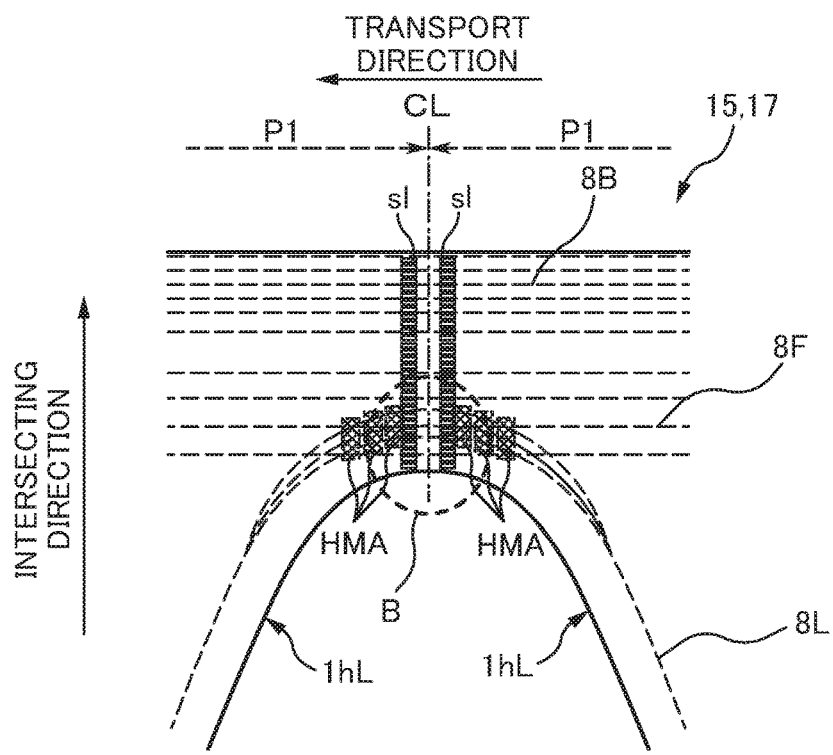
FIG. 10 is a diagram illustrating areas where welded section is formed in welding process.
Figure 11:
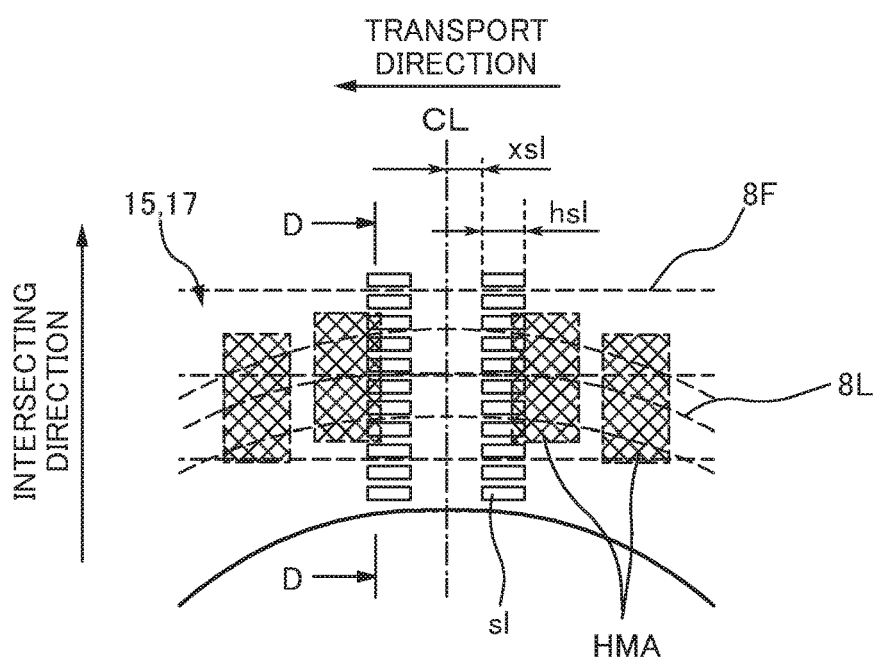
FIG. 11 is a magnified view of the area B in FIG. 10.

FIG. 10 is a diagram illustrating areas where welded section is formed in welding process (S107), and shows the areas corresponding to those of FIG. 5. FIG. 11 is a magnified view of the area B in FIG. 10. While the lower bandlike member 15 and the upper bandlike member 17 being transported along the circumferential surface of the anvil roll 51 of the welding-and-cutting apparatus 50, the members 15 and 17 are welded on the certain area including the cutting position CL at a point-in-time when the anvil brock 511 is positioned facing the sealing block 521. And, the welded sections sl shown in FIGS. 10 and 11 are formed.

The welded sections sl are formed according to the shape of the protruding section 522 of the foregoing sealing block 521. Specifically, on both sides of the cutting position CL in the transport direction, a plurality of rectangular welded sections sl are formed at intervals along the intersecting direction. And, the welded sections sl are formed so as to include a part in which the welded sections sl are not stacked on the adhesion areas HMA within at least partial areas in the transport direction. In FIG. 11, each welded section sl is formed so that the distance from the corresponding cutting position CL to one end section of the welded sections sl in the transport direction (the end section closer to the cutting position) is a value xsl and the width in the transport direction is a value hsl. In the present embodiment, the distance xsl approximately equals 3 to 5 mm, and the width hsl approximately equals 5 to 7 mm. As opposed thereto, the welded sections sl are formed, as illustrated in FIG. 5, so that the distance x from the corresponding cutting position CL to one end section of the adhesion areas HMA in the transport direction (the end section closest to the cutting position) approximately equals 5 to 15 mm. The distance xsl from the cutting position CL to the end section of the welded sections sl in the transport direction is smaller than the distance x from the cutting position CL to the end section of the adhesion areas HMA in the transport direction (xsl<x). That is, the welded sections sl are formed closer to the cutting position CL in the transport direction than the adhesion areas HMA are.

It is desirable that an overlapping part of the welded sections sl and the adhesion areas HMA in the transport direction is as small as possible. The reason is that, if the welded sections sl are formed so as to overlap the entire areas of the adhesion areas HMA, welding strength of the welded sections sl may be insufficient due to the oil of hot-melt adhesive which forms the adhesion areas HMA. Putting of hot-melt adhesive onto the sealing block 521 and/or ultrasonic horn may cause problems such as increase of the number of maintenance operations of the welding-and-cutting apparatus 50, or may prevent continuous manufacturing of the diapers 1. Accordingly, in the present embodiment, the welded sections sl overlap only partial areas of some of the adhesion areas HMA, and this enables the welded sections sl to obtain sufficient welding strength. In the case of FIG. 11, end section areas of the welded sections sl in the transport direction (the end sections away from the cutting position) overlap only end section areas of the adhesion areas HMA in the transport direction (the end sections near the cutting position).

The reason that the welded sections sl and the adhesion areas HMA overlap on partial areas is for fixing more firmly the leg elastic members 8L which adhere to the lower bandlike member 15 (the upper bandlike member 17) while being stretched in the adhesion areas HMA. For example, when the leg elastic members 8L are cut at a cutting position CL in the following cutting process (S108), those leg elastic members 8L contract along the leg openings 1hL in the transport direction (and the intersecting direction) from a portion which has been cut. At this stage, if the leg elastic members 8L insufficiently adhere to the lower bandlike member 15 (the upper bandlike member 17), the leg elastic members 8L are removed (elastic drop-off) from the adhesion areas HMA; consequently, the leg elastic members 8L cannot provide stretchability to the lower bandlike member 15 (the upper bandlike member 17). In this case, when a diaper 1 is worn, a gap is more likely to be formed between a wearer's legs and the leg openings 1hL of the diaper 1, and it is possible that excrement leaks to outside the diaper 1 from the gap. As opposed thereto, the welded sections sl are formed overlapping some parts of the adhesion areas HMA as in the present embodiment. Thereby, the leg elastic members 8L adhere to the lower bandlike member 15 (the upper bandlike member 17) on the adhesion areas HMA. In addition thereto, the leg elastic members 8L become more likely to be held while being sandwiched between the lower bandlike member 15 and the upper bandlike member 17 which are pressurized by the welded sections sl in the thickness direction. This makes the leg elastic members 8L to be less likely to be removed, and can prevent the leg openings 1hL from losing their stretchability.

Figure 12:
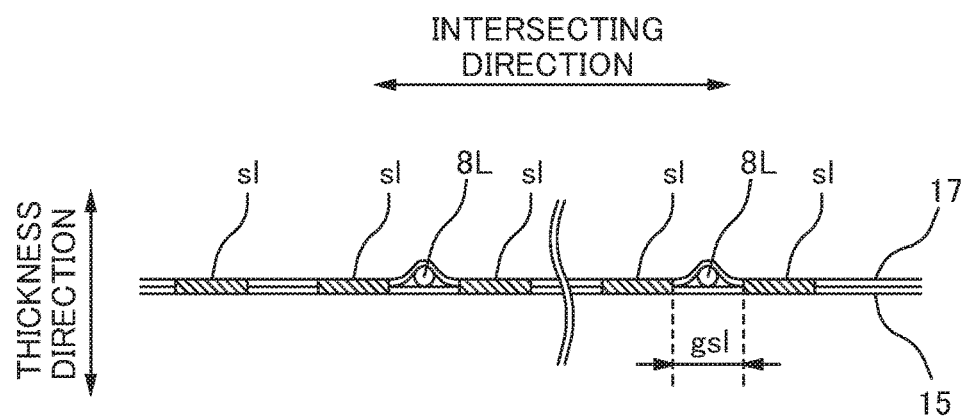
FIG. 12 is a schematic diagram of D-D section in FIG. 11.

In the present embodiment, the welded sections sl are formed so that the distance (gsl) between two welded sections sl and sl adjacent in the intersecting direction is larger than the diameters (thickness) of the leg elastic members 8L. FIG. 12 is a schematic diagram of D-D section in FIG. 11. In FIG. 12, the leg elastic members 8L are placed between the welded sections sl and sl adjacent in the intersecting direction while being sandwiched in the thickness direction between the lower bandlike member 15 and the upper bandlike member 17. If the distance gsl between the welded sections sl and sl is smaller than the diameter of the leg elastic members 8L, a welded section sl is formed by welding at a position in the intersecting direction where at least a part of the welded section sl overlaps a leg elastic member 8L. That is, a part of the leg elastic member 8L is welded to the lower bandlike member 15 (the upper bandlike member 17). In this case, since stretching/contraction force in the transport direction due to the leg elastic member 8L is exerted on the welded section sl, it is possible that contraction of the welded section sl in the transport direction impairs the appearance of the diaper 1 or prevents ensuring sufficient welding strength. As opposed thereto, as in the present embodiment, suppose that the distance gsl between the welded sections sl and sl is larger than the diameter of the leg elastic members 8L. In this case, even when the position where the welded sections sl are to be formed overlaps in the intersecting direction the position where the leg elastic members 8L are placed, if the leg elastic members 8L are pressurized by the anvil brock 511 and the sealing block 521 at the time of welding, the leg elastic members 8L move in the intersecting direction in a pushed manner and are displaced to between the welded sections sl and sl. Thus, the position where the welded sections sl are actually formed and the position of the leg elastic members 8L are less likely to overlap in the intersecting direction. This can prevent the occurrence of the foregoing problems and makes it possible to ensure sufficient welding strength. It can be said that the same applies to the waist elastic members 8B and the fitting-gather elastic members 8F.

In the present embodiment, most of the areas of the lower bandlike member 15 (the upper bandlike member 17) where the welded sections sl are formed are parts in which the surface of nonwoven fabric keeps in good condition. For example, if the adhesion areas HMA are formed on areas where the welded sections sl are to be formed or if the surface of nonwoven fabric is damaged by other means such as a cutter, it is possible that welding is failed which results in insufficient strength of the welded sections. But, in the present embodiment, any treatment to damage the surface is not made on the area between the cutting position CL and the adhesion areas HMA nonwoven fabric. Accordingly, sufficient welding strength can be ensured by normal welding.

The lower bandlike member 15 and the upper bandlike member 17 which have been welded are directly transported on the circumferential surface of the anvil roll 51 of the welding-and-cutting apparatus 50 (see FIG. 8), and are cut along the axial direction (the intersecting direction) at a position where the cutter block 531 of the cutter roll 53 faces the anvil brock 511 (S108). In the present embodiment, the lower bandlike member 15, the upper bandlike member 17 and the elastic members 8B, 8F, 8L are cut together along the cutting position CL.

Figure 13:
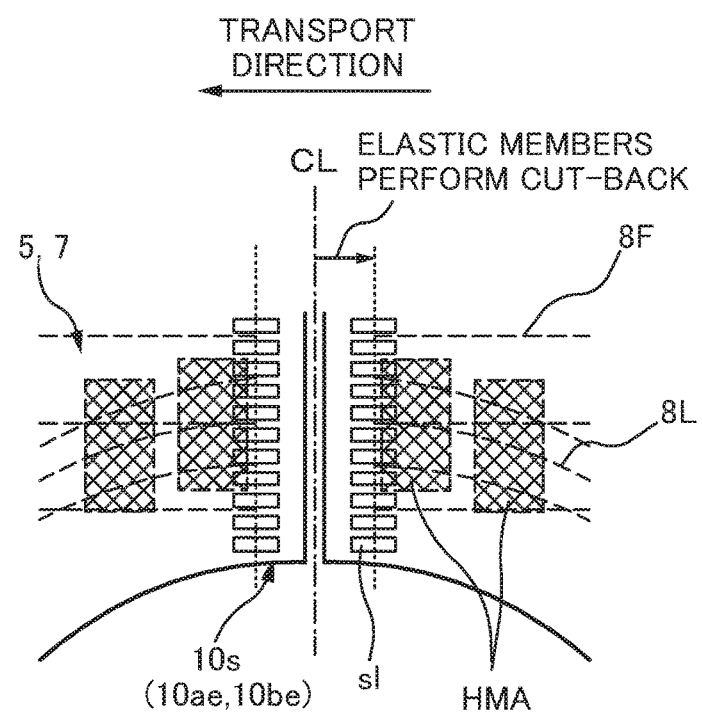
FIG. 13 is a diagram illustrating how a bandlike member and an elastic member are cut in cutting process.

FIG. 13 is a diagram illustrating how the bandlike member and the elastic member are cut in the cutting process (S108), and shows the areas corresponding to those of FIG. 11. In FIG. 13, when cutting along the cutting position CL, the lower exterior member 5 and the upper exterior member 7 which is shaped in the form of underpants are cut and separated from the lower bandlike member 15 and the upper bandlike member 17. Simultaneously, the leg elastic members 8L, which are placed being stretched in a direction having a component parallel to the transport direction, contract from the cut parts towards the adhesion areas HMA, the adhesion areas HMA being formed on both sides of the cutting position CL in the transport direction. This operation is referred to as "cut-back" of an elastic member. In the present embodiment, in an area between the cutting position CL and the adhesion areas HMA (an area having a length x in the transport direction in FIG. 5), the leg elastic members 8L do not adhere to the lower bandlike member 15 and the upper bandlike member 17, or in the area, the leg elastic members 8L adhere at a weak adhesion not to allow stretching/contraction force to be exerted on the lower bandlike member 15 and the upper bandlike member 17. Accordingly, when the leg elastic members 8L perform cut-back, the lower bandlike member 15 and the upper bandlike member 17 do not basically contract, but the leg elastic members 8L contract in the transport direction. In other words, the leg elastic members 8L shift with respect to the transverse end section 10ae and 10ce of the lower bandlike member 15 and the upper bandlike member 17.

As mentioned above, in the configuration of the present embodiment, the leg elastic members 8L are less likely to overlap the welded sections sl in the intersecting direction. Stretching/contraction force caused by the leg elastic members 8L is therefore less likely to be exerted on the welded sections sl. Thus, stretching/contraction force caused by the elastic members is not exerted on the transverse end sections 10s of the diaper 1 (see FIG. 2), and creasing becomes less likely to occur in the area. As a result, the appearance of the diaper 1 and the touch in the area are improved. The leg elastic members 8L which have performed cut-back contract towards the adhesion areas HMA till the end sections of the elastic members are located slightly beyond the end sections of the adhesion areas HMA in the transport direction. But, in the present embodiment, the beyond-end parts of the elastic members are not noticeable, and it is possible to prevent impairing the appearance of the side areas of the diaper 1. This is because a plurality of the welded sections sl are formed at intervals along the intersecting direction between the cutting position CL and the adhesion areas HMA, and because the beyond-end parts are held between the welded sections sl and sl adjacent in the intersecting direction. In this cutting process, it is not necessary for all of a plurality of the leg elastic members 8L to perform cut-back, and the foregoing effects can be achieved even if some of the leg elastic members 8L do not perform cut-back.

In the present embodiment, a plurality of the leg elastic members 8L and other elastic members are each cut on a single cutting position CL. That is, the elastic members are not divided at a plurality of positions in the transport direction, but the elastic members are cut at a single position in the transport direction. More specifically, the elastic members are cut at a single position located between a pair of the adhesion areas HMA which are formed on both sides of the cutting position CL in the transport direction. The elastic members which have been cut perform cut-back and contract to near the end sections of the adhesion areas HMA. Accordingly, the following problems are less likely to occur: a plurality of pieces of the divided elastic members remain in the side parts of the diaper 1 as foreign objects; and the elastic members which have been cut extend beyond the side parts of the diaper 1.

In the present embodiment, since adhesive (hot-melt adhesive) is not applied onto the area between the cutting position CL and the adhesion areas HMA, the leg elastic members 8L do not adhere to the exterior member 10 within the area, and this allows the leg elastic members 8L to easily perform cut-back. In other words, if the leg elastic members 8L can perform cut-back within the area between the cutting position CL and the adhesion areas HMA, adhesive may be applied onto the area. For example, a smaller amount per unit area of adhesive may be applied in the area than that of the adhesion areas HMA. That is, adhesive of a basis weight which allows the leg elastic members 8L to contract (so-called low basis weight) may be applied.

A plurality of the adhesion areas HMA are formed along the position on which the leg elastic members 8L are placed while being arranged in the transport direction. And, elastic drop-off is thereby more likely to be prevented. As mentioned above, in order to increase the fitting on the leg openings 1hL of the diaper 1, the leg elastic members 8L are placed being strongly stretched in a direction having a component parallel to the transport direction. Accordingly, if adhesion to the adhesion areas HMA is insufficient, it is possible that the leg elastic members 8L are removed (elastic drop-off) from the adhesion areas HMA when performing cut-back, which prevents the leg elastic members 8L from producing stretchability in the leg openings 1hL. But, forming a plurality of the adhesion areas HMA in the transport direction can decrease the probability of occurrence of elastic drop-off. For example, in FIG. 5A, three pairs of adhesion areas, namely the adhesion areas HMA1 to HMA 3, are formed along the position on which the leg elastic members 8L are placed while being aligned in the transport direction. Even if elastic drop-off occurs on the adhesion area HMA1, it will often be possible to stop contraction of the leg elastic members 8L at the positions of the adhesion area HMA2 and the adhesion area HMA3 which are formed adjacent to each other. This prevents the leg elastic members 8L from being removed, and exerting stretching/contraction force on the surrounding areas of the leg openings 1hL makes it easier to ensure the fitting of a diaper 1.

The lower exterior member 5 and the upper exterior member 7, which have been cut and separated from the lower bandlike member 15 and the upper bandlike member 17, are transported being absorbed on the anvil roll 51, and are ejected as a single piece of a diaper 1 to outside the welding-and-cutting apparatus 50. Through these processes, the diaper 1 is manufactured.

<Modified Example>

In the foregoing embodiment, the adhesion areas HMA are formed by applying adhesive such as hot-melt type adhesive onto a certain area of the band-like substrates which are being transported (S103 in FIG. 3). However, a method for forming the adhesion areas HMA is not limited thereto. For example, the adhesion areas HMA may be formed as follows: adhesive is applied to certain areas of the leg elastic members 8L and other elastic members, these elastic members being stretched in a direction having a component parallel to the transport direction; and then the leg elastic members 8L and other elastic members are placed on at least either one of the lower bandlike member 15 and the upper bandlike member 17. That is, adhesion-area forming process (S103) and elastic-member placing process (S104) in FIG. 3 may be performed simultaneously.

Applying the adhesive to the elastic members increases adhesion of the elastic members on the adhesion areas HMA, and this makes it easier to prevent problems such as elastic drop-off. If the adhesion-area forming process and the elastic-member placing process are simultaneously performed, the diapers 1 can efficiently be manufactured. However, when applying adhesive only to the elastic members, it should be careful not to displace the positions of the adhesion areas HMA. That is, it is necessary to make adjustment so that the areas in which adhesive is applied to the elastic members and the positions where the elastic members are placed on the band-like substrate are not displaced. Accordingly, it is more preferable that, after adhesive is applied to at least either one of the lower bandlike member 15 and the upper bandlike member 17, adhesive is applied to the elastic members. This is because applying adhesive to the bandlike members 15 and 17 makes it easier to form the adhesion areas HMA precisely at certain positions regardless of the positions where the elastic members are placed.

Second Embodiment

In the second embodiment, a method for manufacturing a disposable diaper consisting of three pieces (diaper 2) will be described.

<Basic Configuration of Diaper 2>

Figure 14:
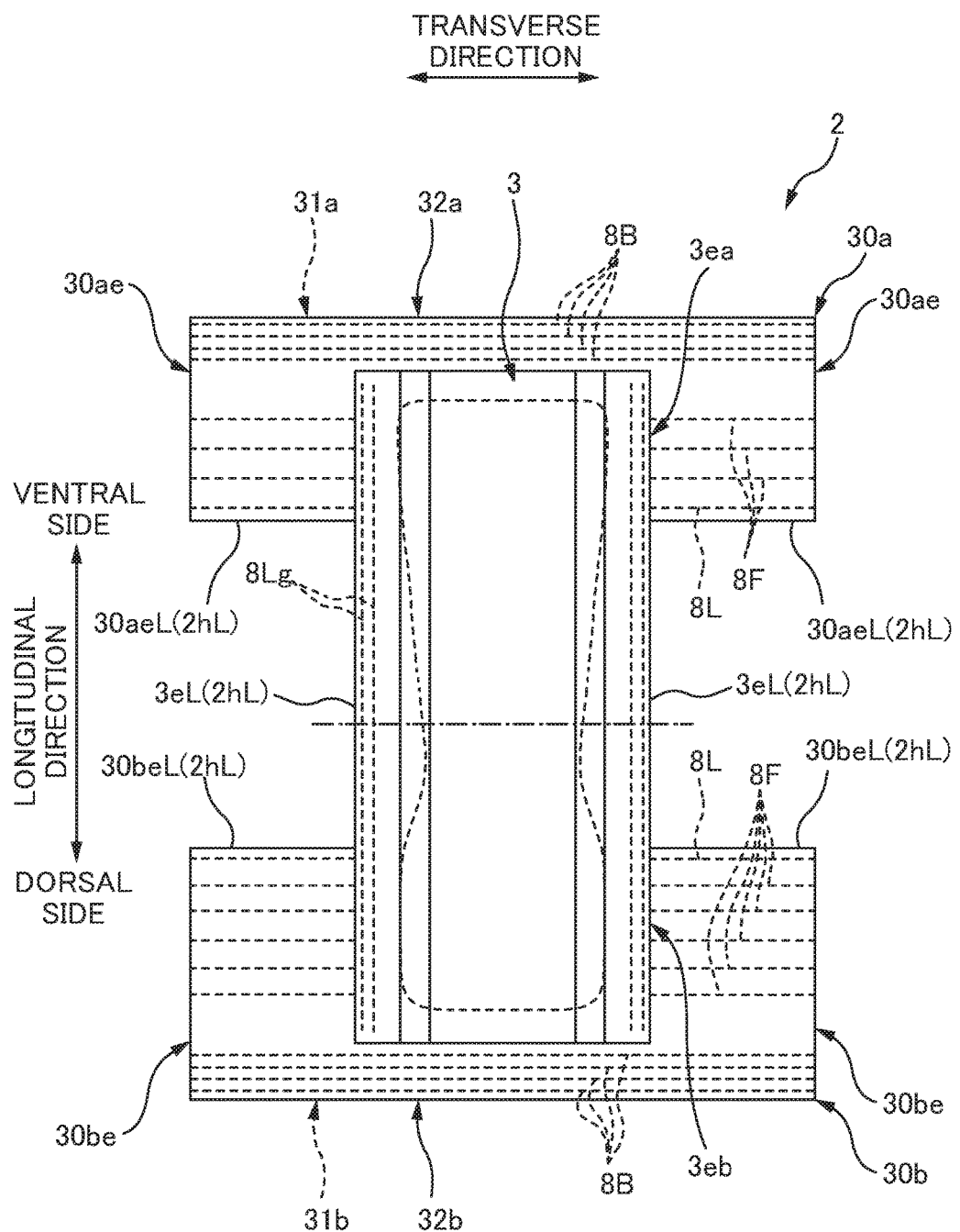
FIG. 14 is a plan view of a disposable diaper 2 which is spread out.

FIG. 14 is a plan view of a disposable diaper 2 which is spread out. In FIG. 14, like the first embodiment, the longitudinal direction and the transverse direction are defined. The thickness direction (not shown) which intersects the longitudinal direction and the transverse direction is also defined.

The diaper 2 which consists of three pieces and is manufactured in the second embodiment includes, as a first component, an absorbent main body 3 which is to be brought into contact with a wearer's crotch and to absorb excrement such as urine. The diaper 2 includes: a ventral band member 30a which covers a wearer's ventral part, as a second component; and a dorsal band member 30b which covers a wearer's dorsal part, as a third component. As for the diaper 2 in FIG. 14 which is spread out, the ventral band member 30a and the dorsal band member 30b are arranged at an interval in the longitudinal direction parallel to each other. In addition, while the absorbent main body 3 bridging between the members 30a and 30b, the lengthwise end sections 3ea and 3eb of the absorbent main body 3 are respectively joined and fixed to the nearest band members 30a and 30b. And, the appearance is in a substantially H shape when viewed from above. The absorbent main body 3 in this state is two-folded on the center in the lengthwise direction (the longitudinal direction). The ventral band member 30a and the dorsal band member 30b which faces each other with being two-folded are joined and connected on a ventral-band-member edge section 30ae and a dorsal-band-member edge section 30be which are to be in contact with wearer's sides (in other words, the end sections in the transverse direction), and thereby these band members 30a and 30b are formed to be a ring. Thus, the diaper 2 which is worn is formed. The leg openings 2hL of the diaper 2 (corresponding to the leg openings 1hL of the diaper 1) are formed by the following sections: the transverse side section 3eL of the absorbent main body 3; the longitudinal inner end section 30aeL of the ventral band member 30a; and the longitudinal inner end section 30beL of the dorsal band member 30b (see FIG. 14).

Both of the ventral band member 30a and the dorsal band member 30b are made of flexible sheets such as nonwoven fabric, and are a sheet member having a substantially rectangular shape when viewed from above. In the second embodiment, the ventral band member 30a is formed by stacking and joining a piece of lower nonwoven fabric 31a and a piece of upper nonwoven fabric 32a. And also, the dorsal band member 30b is formed by stacking and joining a piece of lower nonwoven fabric 31b and a piece of upper nonwoven fabric 32b. While being stretched along the transverse direction, the waist elastic members 8B, the fitting-gather elastic members 8F and the leg elastic members 8L are placed between the lower nonwoven fabric 31a and 31b and the upper nonwoven fabric 32a and 32b. Stretchability in the transverse direction is thereby provided to the ventral band member 30a and the dorsal band member 30b of the diaper 2. The waist elastic members 8B are respectively placed at outer positions in the longitudinal direction within the ventral band member 30a and the dorsal band member 30b, and the fitting-gather elastic members 8F are respectively placed at inner positions in the longitudinal direction with respect to the positions of the waist elastic members 8B. The leg elastic members 8L are placed at inner positions in the longitudinal direction with respect to the fitting-gather elastic members 8F, and are arranged along the longitudinal inner end section of the ventral band member 30a and the dorsal band member 30b. In FIG. 14, as the leg elastic member 8L, illustrated is only the elastic member which is placed on the innermost positions in the longitudinal direction along the longitudinal inner end section 30aeL of the ventral band member 30a and the longitudinal inner end section 30beL of the dorsal band member 30b. However, a plurality of the leg elastic members 8L may be respectively disposed of the ventral band member 30a and the dorsal band member 30b. On the transverse end sections of the absorbent main body 3, leg-gather elastic members 8Lg are placed while being stretched along the longitudinal direction. And, stretchability in the longitudinal direction is thereby provided to the absorbent main body 3.

In the diaper 2 consisting of three pieces, stretchability is provided to the leg openings 2hL by the following parts: some of the leg elastic members 8L which are placed along the longitudinal inner end sections 30aeL and 30beL of the band member; and some of the leg-gather elastic members 8Lg which are placed along the transverse side section 3eL of the absorbent main body 3. Thus, a gap becomes less likely to be formed between a wearer's legs and the leg openings 2hL, and this can prevent excrement from leaking to outside the diaper 2. The following description will be made as if the leg elastic members 8L placed along the longitudinal inner end sections 30aeL and 30beL of the band members 30a and 30b correspond to the leg elastic members 8L in the first embodiment.

The detailed description of components of the diaper 2 is omitted because a disposable diaper consisting of three pieces itself is publicly known.

<Method for Manufacturing Diaper 2>

A method for manufacturing diapers 2 of the second embodiment will be described.

Figure 15:
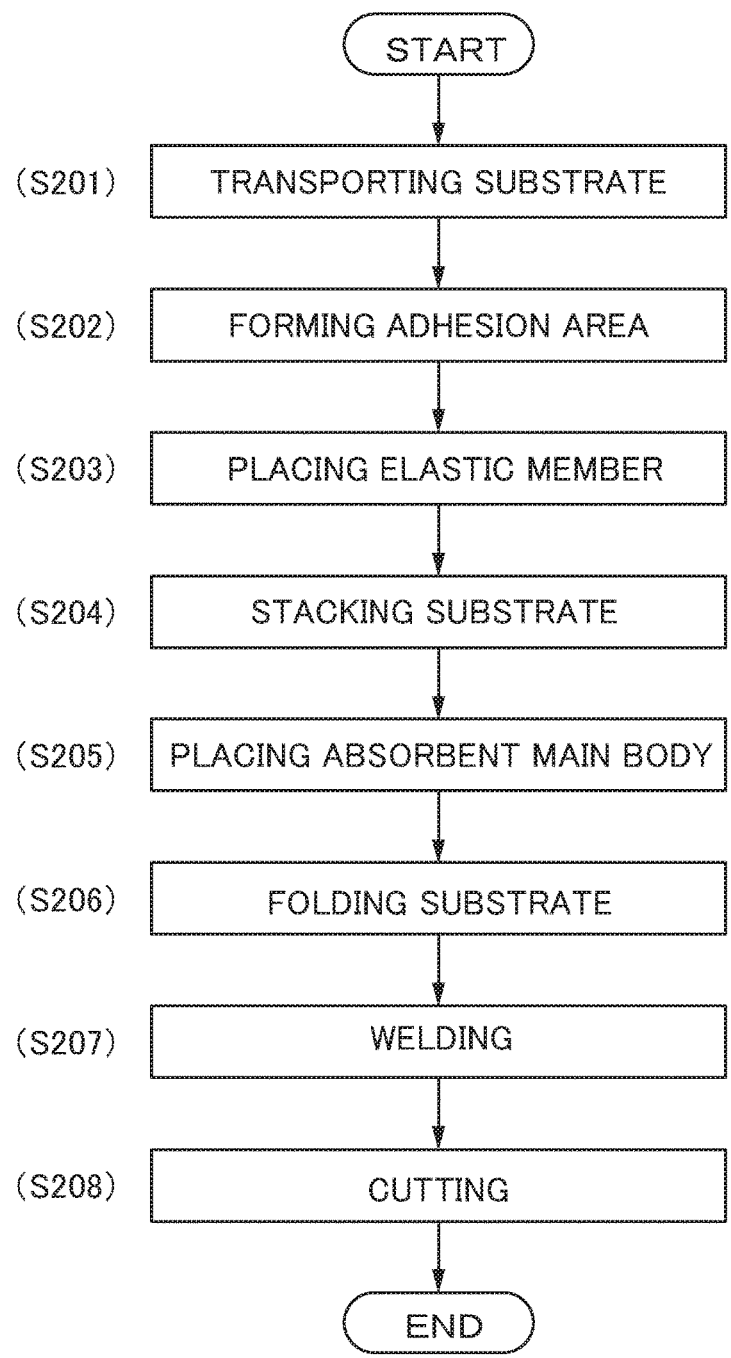
FIG. 15 is a flow chart of processes for manufacturing the diapers 2 in the second embodiment.

FIG. 15 is a flow chart of processes for manufacturing the diapers 2 in the second embodiment. The diapers 2 are continuously manufactured by performing processes (S201 to S208 in FIG. 15) in a manufacturing line. The processes S201 to S208 in the second embodiment are basically the same as the processes S101 to S108 in the first embodiment.

First, the substrate of the diapers 2 is transported along a certain transport direction at a certain transport speed (S201). The "substrate of the diapers 2" is composed of a ventral bandlike member 31a1 (a ventral bandlike member 32a1) and a dorsal bandlike member 31bl (a dorsal bandlike member 32bl). The ventral bandlike member 31a1 (the ventral bandlike member 32a1) is a member in which a plurality of pieces of the lower nonwoven fabric 31a (the upper nonwoven fabric 32a) are continuously linked in the transverse direction; the lower nonwoven fabric 31a (the upper nonwoven fabric 32a) constitutes the ventral band member 30a. Also, the dorsal bandlike member 31bl (the dorsal bandlike member 32bl) is a member in which a plurality of pieces of the lower nonwoven fabric 31b (the upper nonwoven fabric 32b) are continuously linked in the transverse direction; the lower nonwoven fabric 31b (the upper nonwoven fabric 32b) constitutes the dorsal band member 30b. These members are transported in the transport direction while the members each keep their position in relation to each other at certain distances in the intersecting direction. The definitions of "the transport direction" and "intersecting direction" are the same as in the first embodiment.

Figure 16:
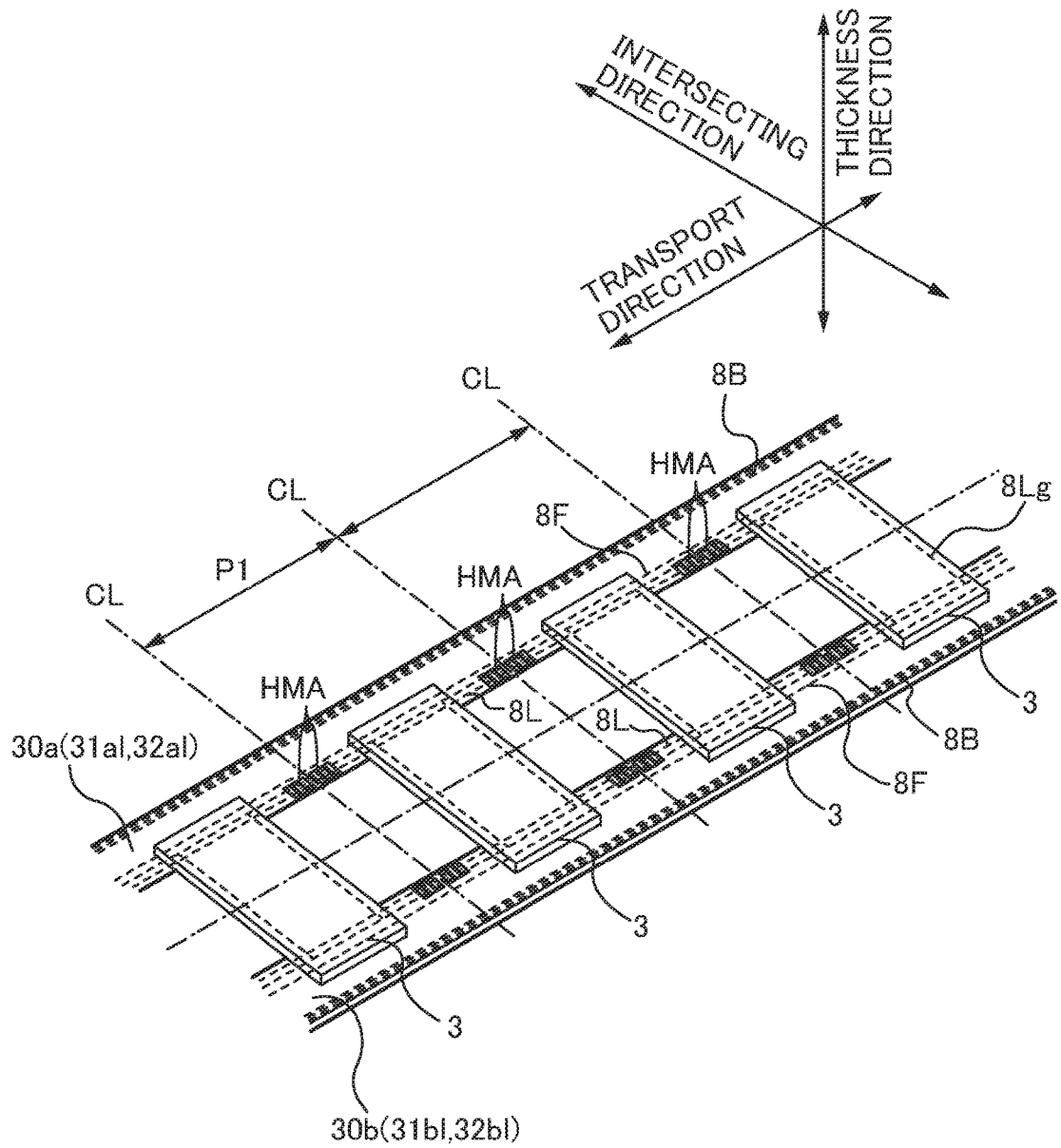
FIG. 16 is a diagram illustrating how the substrate of the diapers 2 is transported in the transport direction.

FIG. 16 is a diagram illustrating how the substrate of the diapers 2 is transported in the transport direction. FIG. 16 shows a state after the absorbent main body 3 bridges and is joined between the ventral band member 30a and the dorsal band member 30b in the process S205. In the second embodiment, as in the first embodiment, a cutting position CL is defined which is to be sections 30ae and 30be serving as the transverse end sections of a diaper 2 which is shaped in the form of underpants. Also, in the second embodiment, the operations of the processes are controlled based on the cutting position CL.

First, hot-melt type adhesive is put on certain areas of the substrate which is being transported, and the adhesion areas HMA are formed (S202). The areas where the adhesion areas HMA are formed are substantially the same as in the first embodiment, and the adhesion areas HMA are formed in certain areas on both sides of the cutting position CL in the transport direction substrate. In the second embodiment, one or more adhesion areas HMA are formed along the position on which the leg elastic members 8L are placed.

Thereafter, the leg elastic members 8L (with the waist elastic members 8B and the fitting-gather elastic members 8F) are placed while being stretched in the transport direction (S203). At this stage, the elastic members 8L, 8B, and 8F are placed so that the partial areas of the elastic members 8L, 8B, and 8F respectively overlap the adhesion areas HMA. And, the elastic members 8L, 8B, and 8F adhere to the ventral bandlike member 31al and the dorsal bandlike member 31bl on the overlapping area. After the elastic members are placed, the ventral bandlike member 32al is stacked on the ventral bandlike member 31al and the elastic members 8L, 8B, and 8F (S204). Accordingly, the leg elastic members 8L, and the waist elastic members 8B, the fitting-gather elastic members 8F are fixed to the substrates (the ventral bandlike member 31al and the ventral bandlike member 32*al*) while being sandwiched in the thickness direction between the substrates. Similarly, the dorsal bandlike member 32*bl* is stacked on the dorsal bandlike member 31*bl* and the elastic members 8L, 8B, and 8F. In the foregoing processes, the lower nonwoven fabric may be stacked on the upper nonwoven fabric which is being transported.

Subsequently, the absorbent main body 3 is placed and joined so as to bridge between the ventral band member 30*a* and the dorsal band member 30*b* (S205). With hot-melt adhesive, etc., the ventral band member 30*a* and the dorsal band member 30*b* is joined to the absorbent main body 3. FIG. 16 shows a state after the absorbent main body 3 has been joined in this process. The absorbent main body 3 is folded on the center in the intersecting direction so that the ventral band member 30*a* and the dorsal band member 30*b* are stacked in the thickness direction (S206).

Thereafter, the ventral band member 30*a* and the dorsal band member 30*b* which are stacked are welded on the certain area (S207). The operation of the welding process is substantially the same as in the first embodiment, and is performed using the welding-and-cutting apparatus 50. Thus, a plurality of the welded sections sl are formed at intervals along the intersecting direction so that some of the welded sections partially overlap the adhesion areas HMA. In the second embodiment, as described in the first embodiment, welding can be performed so that sufficient welding strength is ensured.

Finally, the ventral band member 30*a*, the dorsal band member 30*b* and the leg elastic members 8L (and the waist elastic members 8B and the fitting-gather elastic members 8F) are cut together at the cutting position CL (S208). The operation of cutting process is also substantially the same as in the first embodiment, and the leg elastic members 8L which are stretched in the transport direction perform cutback from a portion which has been cut towards the adhesion areas HMA. Accordingly, stretching/contraction force caused by the leg elastic members 8L is not exerted on the transverse end sections 30*ae* and 30*be* of the diaper 2 (see FIG. 14), and creasing becomes less likely to occur in the area. As a result, the appearance and the touch of the diaper 2 are improved. If a plurality of the adhesion areas HMA is formed along the position on which the leg elastic members 8L are placed, the leg elastic members 8L becomes less likely to be removed.

Other Embodiments

While the embodiments according to the invention are described above, the above-mentioned embodiments are provided for facilitating the understanding of the invention, and are not to be interpreted as limiting the invention. As a matter of course, the invention can be altered and improved without departing from the gist thereof and the invention includes equivalent thereof. For example, the invention can be altered as described below.

In the foregoing embodiment, after the elastic members are placed on the lower substrate (e.g., the lower bandlike member 15) which is being transported, the exterior member of an absorbent article is formed by stacking on and joining to the upper substrate (e.g., the upper bandlike member 17). However, a process for forming the exterior member is not limited thereto. For example, the elastic members may be placed between the lower substrate and the upper substrate which are being transported in parallel in a state in which these substrates faces each other. In any way, a method for manufacturing an absorbent article according to the present application can apply to any configuration for forming an exterior member in which the elastic members are placed, the elastic members being stretched and sandwiched between a first substrate and a second substrate.

In the foregoing embodiment, using the welding-and-cutting apparatus 50, the welding process (S106, for example) and the cutting process (S107) are performed as a series of operations. However, these processes may be performed individually. For example, the following configuration is acceptable. Using a first anvil roll and a second anvil roll instead of the anvil roll 51 of the welding-and-cutting apparatus 50, the welding process is performed while the band-like substrate being transported by the first anvil roll. And then, the cutting process is performed while the band-like substrate being transported by the second anvil roll. In addition, a configuration in which the welding process alone is performed with the anvil roll and the cutting process is individually performed with another cutting device may be employed. Further, any other configuration may be employed depending on the place or conditions of a manufacturing line.

In the foregoing embodiment, nonwoven fabric is provided as an example of the materials of the lower exterior member 5 and the upper exterior member 7. However, the materials are not limited to nonwoven fabric. For example, woven fabric or any other sheet member except for woven fabric may also be used.

In the foregoing embodiment, rubber thread is provided as an example of the elastic members 8. However, this invention is not limited thereto. For example, band-like rubber may be used as the elastic members 8, and band-like nonwoven fabric with stretchability or band-like resin film with stretchability may also be used.

REFERENCE SIGNS LIST 1 diaper (absorbent article),
1*h*B waist opening, 1*h*L leg opening,
2 diaper (absorbent article)
2*h*L leg opening,
3 absorbent main body, 3*b* back face sheet, 3*d* absorbent body,
3*s* top face sheet,
3*ea* end section, 3*eb* end section, 3*e*L transverse side section,
5 lower exterior member,
7 upper exterior members,
8B waist elastic member, 8F fitting-gather elastic member,
8L, 8La, 8Lb leg elastic member, 8Lg leg-gather elastic member,
10 exterior members,
10A ventral part, 10*ae* transverse end section,
10B crotch part,
10C dorsal part, 10*ce* transverse end section,
10*e* edge section, 10*e*L edge section, 10*s* transverse end section,
15 lower bandlike member,
17 upper bandlike members,
30*a* ventral band member, 30*ae* ventral-band-member edge section,
30*ae*L longitudinal inner end section,
30*b* dorsal band member, 30*be* dorsal-band-member edge section,
30*be*L longitudinal inner end section,
31*a* lower nonwoven fabric, 31*al* ventral bandlike member,
31*b* lower nonwoven fabric, 31*bl* dorsal bandlike member,
32*a* upper nonwoven fabric, 32*al* ventral bandlike member,
32*b* upper nonwoven fabric, 32*bl* dorsal bandlike member,
50 welding-and-cutting apparatus,
51 anvil roll, 511 anvil brock, 52 sealing roll, 521 sealing block, 522 protruding section, 522a rectangular portion,
53 cutter roll, 531 cutter block,
54 transportation-assisting roll,
CL cutting position,
HMA, HMA1, HMA2, HMA3 adhesion area,
sl welded section

The invention claimed is:

1. A method for continuously manufacturing an absorbent article,
the absorbent article being a pull-on absorbent article
that has a longitudinal direction and a transverse direction intersecting the longitudinal direction, and
that includes
a lower exterior member located on a side towards a wearer's garment,
an upper exterior member stacked on the lower exterior member from a side towards a wearer's skin,
an absorbent main body stacked on the upper exterior member from the side towards a wearer's skin, for absorbing excrement,
the method, comprising:
while a lower bandlike member and an upper bandlike member are transported in a transport direction that is along the transverse direction,
the lower bandlike member including the lower exterior members that continue in a band-like manner in the transverse direction,
the upper bandlike member including the upper exterior members that continues in a band-like manner in the transverse direction,
a process in which, when the lower exterior member and the upper exterior member are cut and separated from the lower bandlike member and the upper bandlike member,
a cutting position is determined, and
an adhesion area is formed by putting adhesive on each side of the cutting position in the transport direction, of at least either one of the lower bandlike member and the upper bandlike member,
the cutting position being to serve as end sections of the lower exterior member and the upper exterior member in the transverse direction;
a process in which
a plurality of leg elastic members are placed on at least either one of the lower bandlike member and the upper bandlike member so that a part of each of the leg elastic members overlaps the adhesion area,
the leg elastic members being stretched in a direction having a component parallel to the transport direction,
the leg elastic members being provided along a leg opening of the pull-on absorbent article;
a process in which
the lower bandlike member and the upper bandlike member are stacked such that the leg elastic members being sandwiched between the lower and upper bandlike members, and
the upper bandlike member adheres to the lower bandlike member and the leg elastic members on the adhesion area;
a process in which
the lower bandlike member and the upper bandlike member are folded on a center portion in an intersecting direction so that the upper bandlike member is located inside the lower bandlike member,
the intersecting direction intersecting the transport direction;
a process in which
a welded section on which the folded lower bandlike member and the folded upper bandlike member are to be welded to each other is formed on each side of the cutting position in the transport direction;
a process in which
the lower bandlike member, the upper bandlike member and the leg elastic members are cut together on the cutting position,
the lower exterior member and the upper exterior member which are shaped in the form of underpants are cut and separated from the lower bandlike member and the upper bandlike member,
at least some of the plurality of leg elastic members that are stretched in the direction having the component parallel to the transport direction contract in the transport direction towards the adhesion area from positions at which the at least some of the plurality of leg elastic members are cut,
the contraction being performed while the at least some of the plurality of leg elastic members shifting relative to the lower exterior member and the upper exterior member,
wherein
the heat-welded section does not overlap the adhesion area within at least a partial area along the transport direction,
adhesive is not applied on an area in the transport direction between the cutting position and the adhesion area,
a plurality of the heat-welded sections that comprise multiple heat bonding parts, the multiple heat bonding parts being spaced apart from each other in the intersecting direction,
a distance in the intersecting direction between two adjacent ones of the multiple heat bonding parts is larger than a diameter of the leg elastic member,
a dimension in the intersecting direction of each of the two adjacent ones of the multiple heat bonding parts is shorter than half a distance between transverse end sections of two leg elastic members that are adjacent one another in the intersecting direction,
a plurality of the adhesion areas are formed being aligned in the transport direction along the position on which the leg elastic members are placed,
the plurality of the adhesion areas are formed at an interval so that a pair of the adhesion areas being adjacent in the transport direction overlap each other in the intersecting direction,
the interval being smaller than widths of the adhesion areas in the transport direction.

2. A method for manufacturing an absorbent article according to claim 1, wherein
a distance between the cutting position and one end section of the heat-welded section in the transport direction is shorter than a distance between the cutting position and one end section of the adhesion area in the transport direction,
the one end section of the heat-welded section being closer to the cutting position than the other end section is,
the one end section of the adhesion area being closer to the cutting position than the other end section is.

3. A method for manufacturing an absorbent article according to claim 1, wherein the process in which the adhesion area is formed is performed
by placing the leg elastic members on at least either one of the lower bandlike member and the upper bandlike member,
adhesive being applied to the leg elastic members on a certain area while the leg elastic members being stretched in the direction having the component parallel to the transport direction.

4. A method for manufacturing an absorbent article according to 1, wherein
the leg elastic members are cut at a single position located between a pair of the adhesion areas,
the leg elastic members being stretched in the direction having the component parallel to the transport direction,
the adhesion areas being respectively formed on both side of the cutting position in the transport direction, and
the leg elastic members contract in the transport direction towards the adhesion areas from positions at which the leg elastic members are cut.

5. A method for continuously manufacturing an absorbent article,
the absorbent article being a pull-on absorbent article
that has a longitudinal direction and a transverse direction intersecting the longitudinal direction, and
that includes
a lower exterior member located on a side towards a wearer's garment,
an upper exterior member stacked on the lower exterior member from a side towards a wearer's skin,
an absorbent main body stacked on the upper exterior member from the side towards a wearer's skin, for absorbing excrement,
the method, comprising:
while a lower bandlike member and an upper bandlike member are transported in a transport direction that is along the transverse direction,
the lower bandlike member including the lower exterior members that continue in a band-like manner in the transverse direction,
the upper bandlike member including the upper exterior members that continues in a band-like manner in the transverse direction,
a process in which, when the lower exterior member and the upper exterior member are cut and separated from the lower bandlike member and the upper bandlike member,
a cutting position is determined, and
an adhesion area is formed by putting adhesive on each side of the cutting position in the transport direction, of at least either one of the lower bandlike member and the upper bandlike member,
the cutting position being to serve as end sections of the lower exterior member and the upper exterior member in the transverse direction;
a process in which
a plurality of leg elastic members are placed on at least either one of the lower bandlike member and the upper bandlike member so that a part of each of the leg elastic members overlaps the adhesion area,
the leg elastic members being stretched in a direction having a component parallel to the transport direction,
the leg elastic members being provided along a leg opening of the pull-on absorbent article;
a process in which
the lower bandlike member and the upper bandlike member are stacked such that the leg elastic members being sandwiched between the lower and upper bandlike members, and
the upper bandlike member adheres to the lower bandlike member and the leg elastic members on the adhesion area;
a process in which
the lower bandlike member and the upper bandlike member are folded on a center portion in an intersecting direction so that the upper bandlike member is located inside the lower bandlike member,
the intersecting direction intersecting the transport direction;
a process in which
a heat-welded section on which the folded lower bandlike member and the folded upper bandlike member are to be heat-welded to each other is formed on each side of the cutting position in the transport direction;
a process in which
the lower bandlike member, the upper bandlike member and the leg elastic members are cut together on the cutting position,
the lower exterior member and the upper exterior member which are shaped in the form of underpants are cut and separated from the lower bandlike member and the upper bandlike member,
at least some of the plurality of leg elastic members that are stretched in the direction having the component parallel to the transport direction contract in the transport direction towards the adhesion area from positions at which the at least some of the plurality of leg elastic members are cut,
the contraction being performed while the at least some of the plurality of leg elastic members shifting relative to the lower exterior member and the upper exterior member,
wherein
the heat-welded section does not overlap the adhesion area within at least a partial area along the transport direction,
adhesive is not applied on an area in the transport direction between the cutting position and the adhesion area,
a plurality of the heat-welded sections that comprise multiple heat bonding parts, the multiple heat bonding parts being spaced apart from each other in the intersecting direction,
a distance in the intersecting direction between two adjacent ones of the multiple heat bonding parts is larger than a diameter of the leg elastic member,
a dimension in the intersecting direction of each of the two adjacent ones of the multiple heat bonding parts is shorter than half a distance between transverse end sections of two leg elastic members that are adjacent one another in the intersecting direction,
a plurality of the adhesion areas are formed being aligned in the transport direction along the position on which the leg elastic members are placed, and
when, among the plurality of the adhesion areas of each pull-on absorbent article,
a transversely outermost adhesion area is defined as a first adhesion area and a transversely second outermost adhesion area, next to the first adhesion area, is defined as a second adhesion area, a longitudinal upper end of the first adhesion area is located above a longitudinal upper end of the second adhesion area, and a longitudinal lower end of the first adhesion area is located between the longitudinal upper end of the second adhesion area and a longitudinal lower end of the second adhesion area.

* * * * *